United States Patent [19]
Gaber

[11] Patent Number: 6,027,518
[45] Date of Patent: Feb. 22, 2000

[54] SEIZING INSTRUMENT

[76] Inventor: Benny Gaber, 29 Oren Street, Apt. 46, Haifa, Israel, 34735

[21] Appl. No.: 08/952,895
[22] PCT Filed: May 29, 1996
[86] PCT No.: PCT/US96/07863
   § 371 Date: Apr. 6, 1998
   § 102(e) Date: Apr. 6, 1998
[87] PCT Pub. No.: WO96/38197
   PCT Pub. Date: Dec. 5, 1996

[30]    Foreign Application Priority Data

May 30, 1995  [IL]  Israel ........................................ 113922

[51] Int. Cl.⁷ ........................... A61M 29/00; A61B 17/00
[52] U.S. Cl. ............................................ 606/198; 604/105
[58] Field of Search ................... 606/1, 191, 198, 606/200, 207; 604/104–107

[56]    References Cited

U.S. PATENT DOCUMENTS

| | | |
|---|---|---|
| 4,043,346 | 8/1977 | Mobley et al. ................. 606/198 |
| 4,393,872 | 7/1983 | Reznik et al. .................. 606/206 |
| 4,497,325 | 2/1985 | Wedel . |
| 4,654,028 | 3/1987 | Suma . |
| 4,747,833 | 5/1988 | Kousai et al. . |
| 4,781,682 | 11/1988 | Patel . |
| 4,781,690 | 11/1988 | Ishida et al. . |
| 5,002,556 | 3/1991 | Ishida et al. . |
| 5,062,415 | 11/1991 | Weatherby et al. . |
| 5,139,511 | 8/1992 | Gill et al. . |
| 5,169,397 | 12/1992 | Sakashita et al. . |
| 5,195,506 | 3/1993 | Hulfish . |
| 5,197,971 | 3/1993 | Bonutti . |
| 5,245,987 | 9/1993 | Redmond et al. . |
| 5,287,848 | 2/1994 | Cubb et al. . |
| 5,330,501 | 7/1994 | Tovey et al. ................. 604/105 |
| 5,865,802 | 2/1999 | Yoon et al. .................. 604/107 |

FOREIGN PATENT DOCUMENTS

| | | |
|---|---|---|
| 0 643 980 | 3/1995 | European Pat. Off. . |
| 568069 | 12/1972 | Switzerland . |
| 459218 | 1/1977 | U.S.S.R. . |
| 1618396 | 1/1991 | U.S.S.R. . |
| WO 93/15699 | 8/1993 | WIPO . |
| WO 94/21179 | 9/1994 | WIPO . |

*Primary Examiner*—Michael Buiz
*Assistant Examiner*—William W. Lewis
*Attorney, Agent, or Firm*—Helfgott & Karas, PC.

[57]    ABSTRACT

This invention is an instrument for seizing walls of a body cavity including a first portion (22) and a second portion (30), the second portion being insertable into the cavity and being reversibly deformable from a first (FIG. 5A) to a second (FIG. 5B) configuration while inside the cavity, the first portion being operative to reversibly deform the second portion from the first to the second configuration, the second portion when in the second configuration being operative to seize the walls of the cavity.

11 Claims, 22 Drawing Sheets

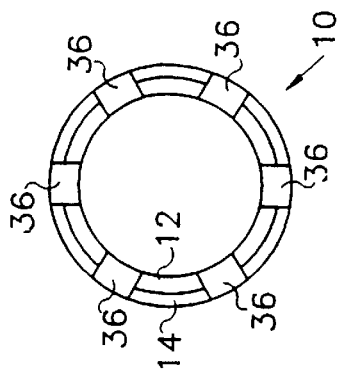
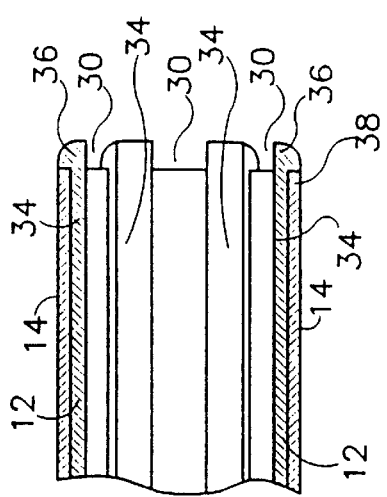
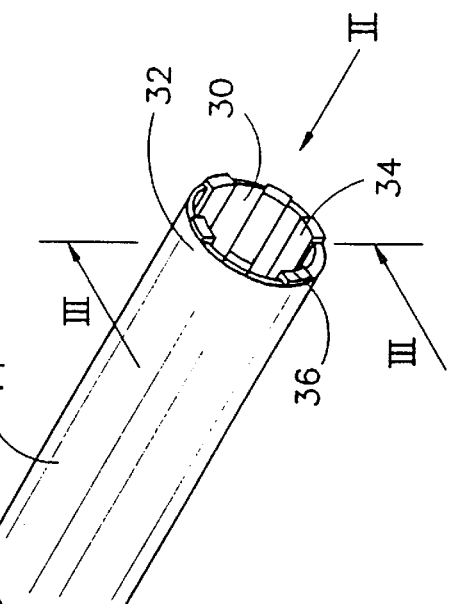
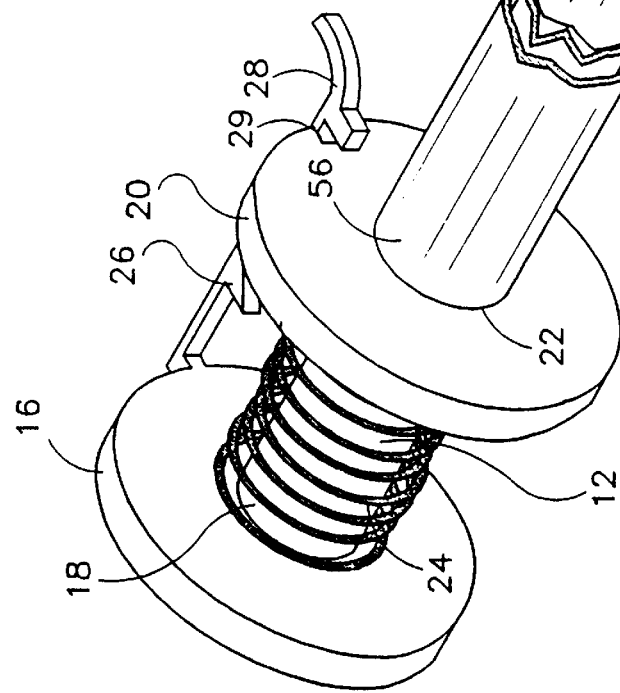

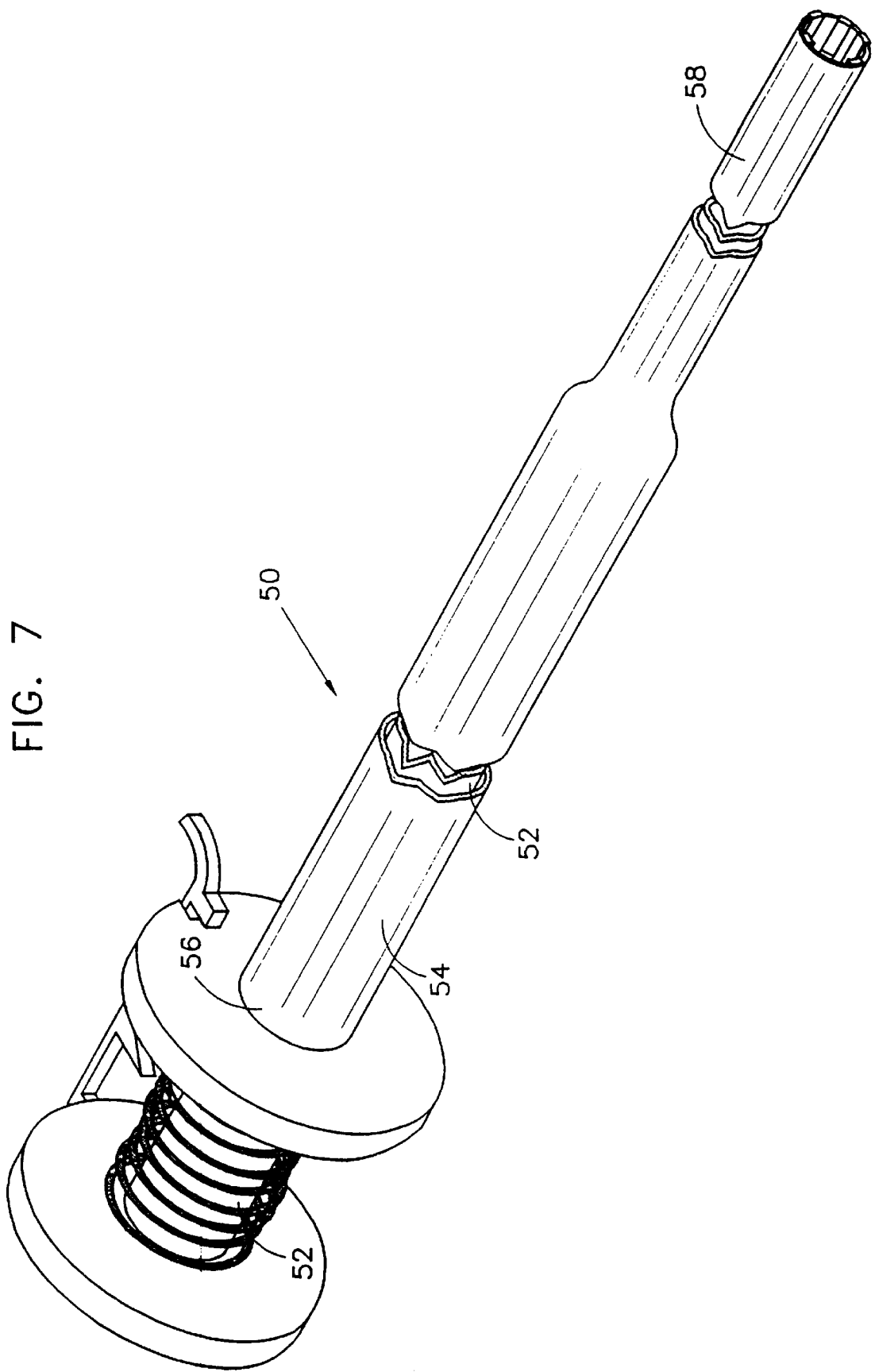

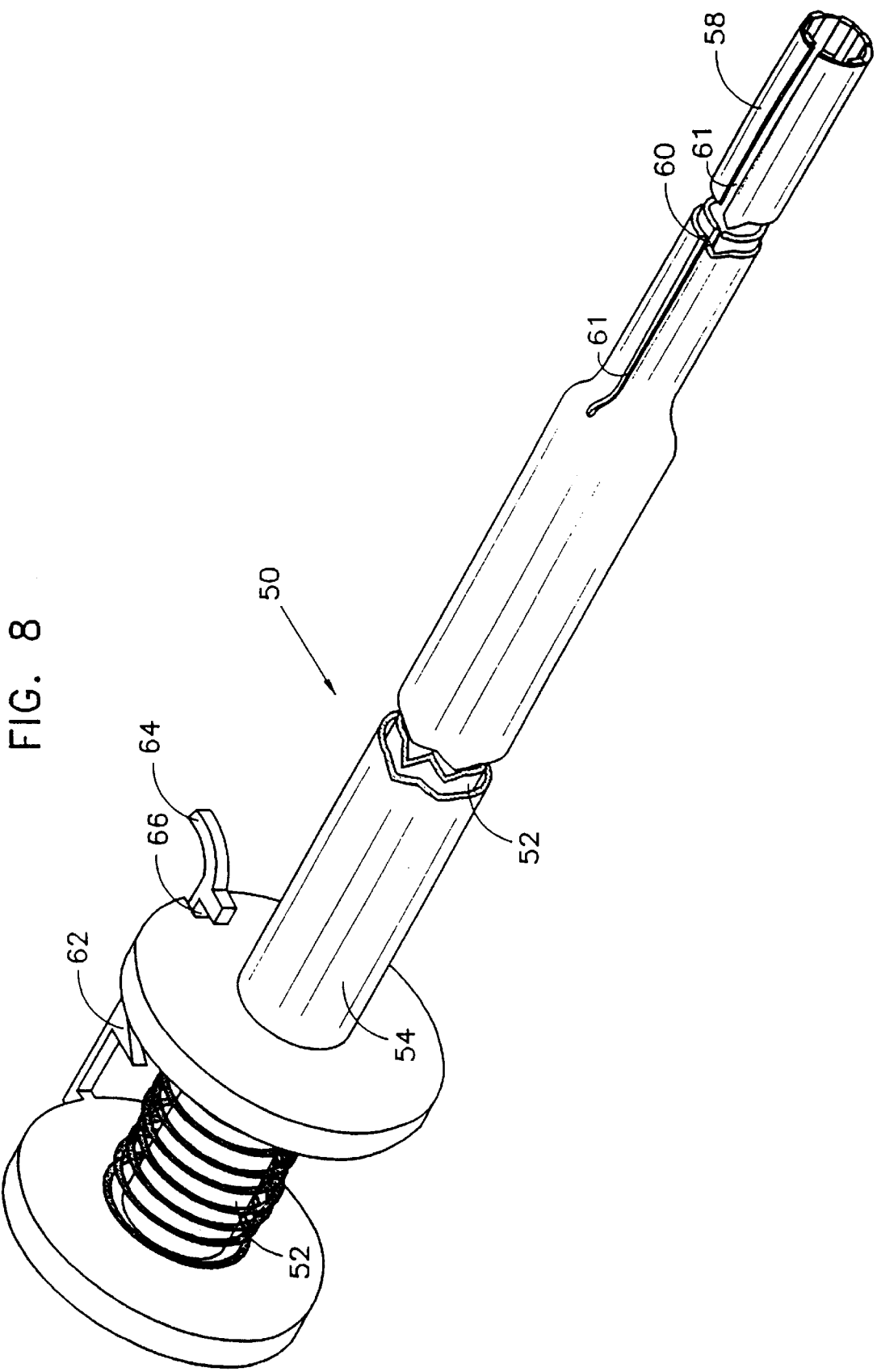

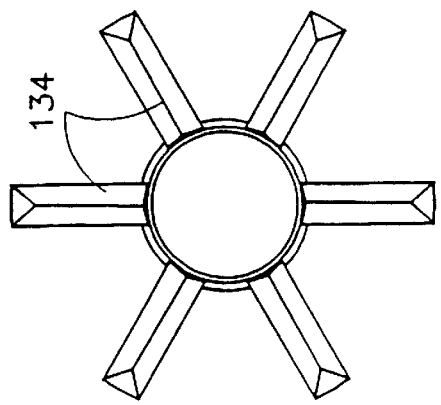
FIG. 13
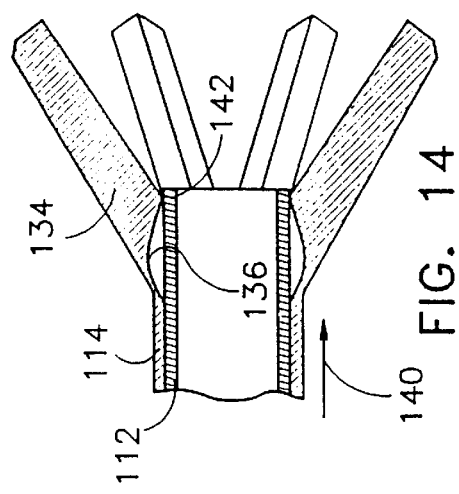
FIG. 14
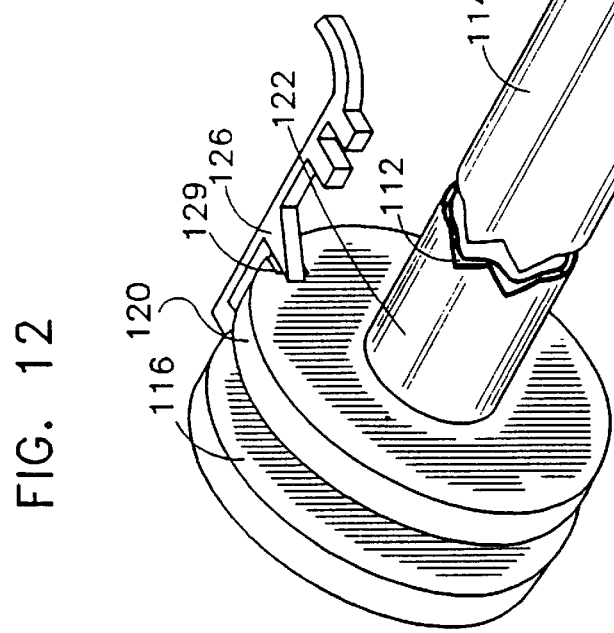
FIG. 12
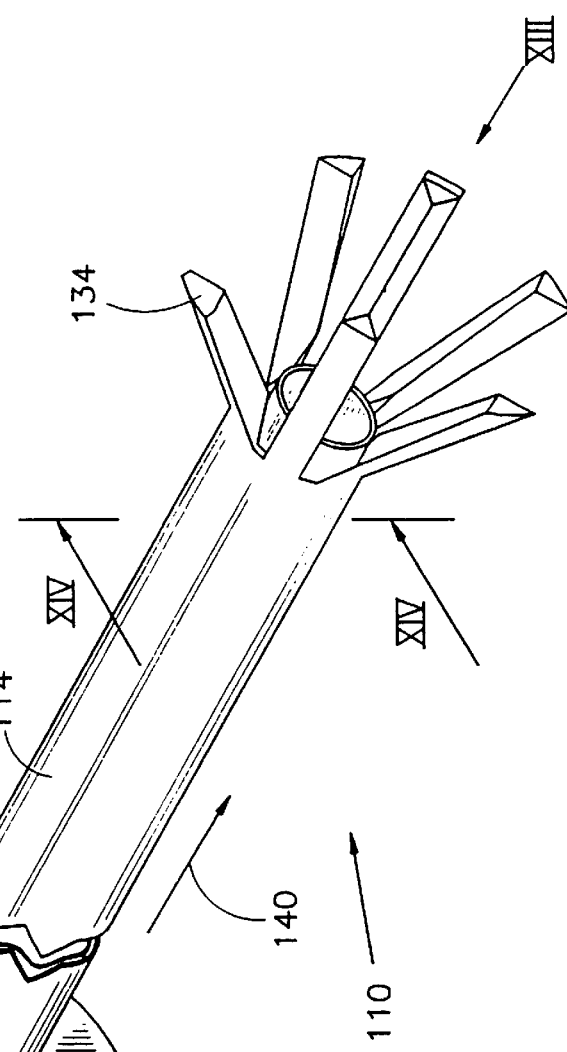

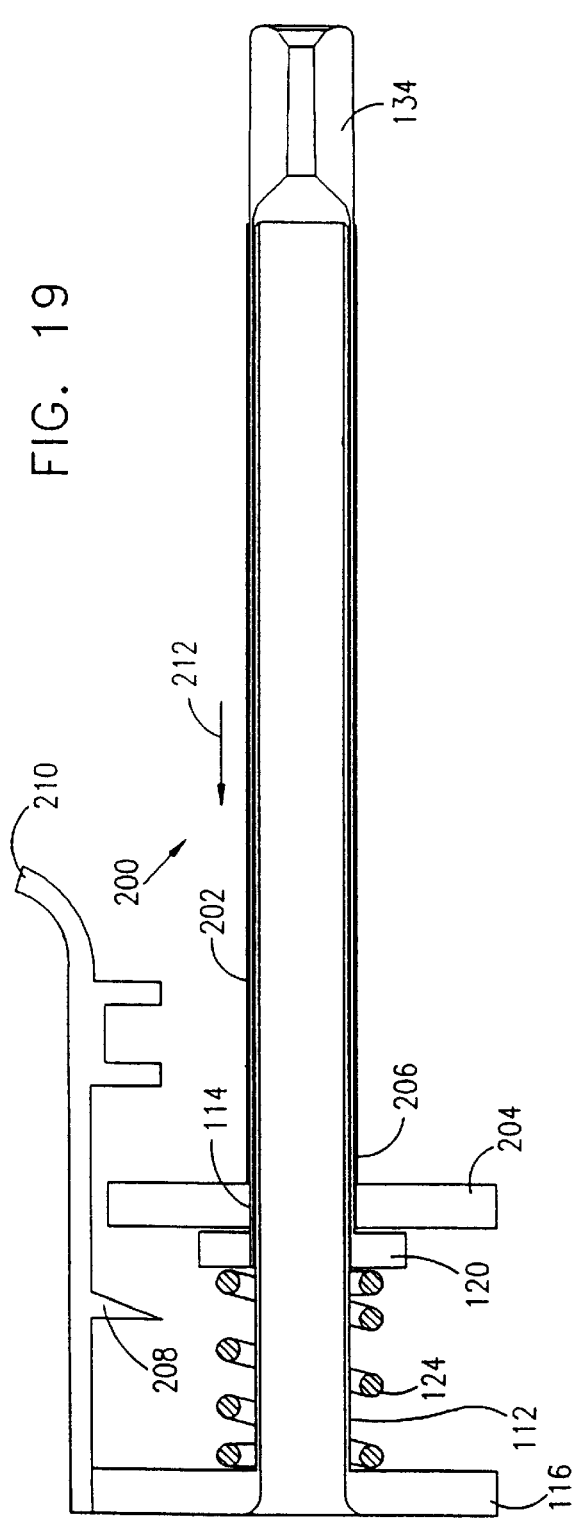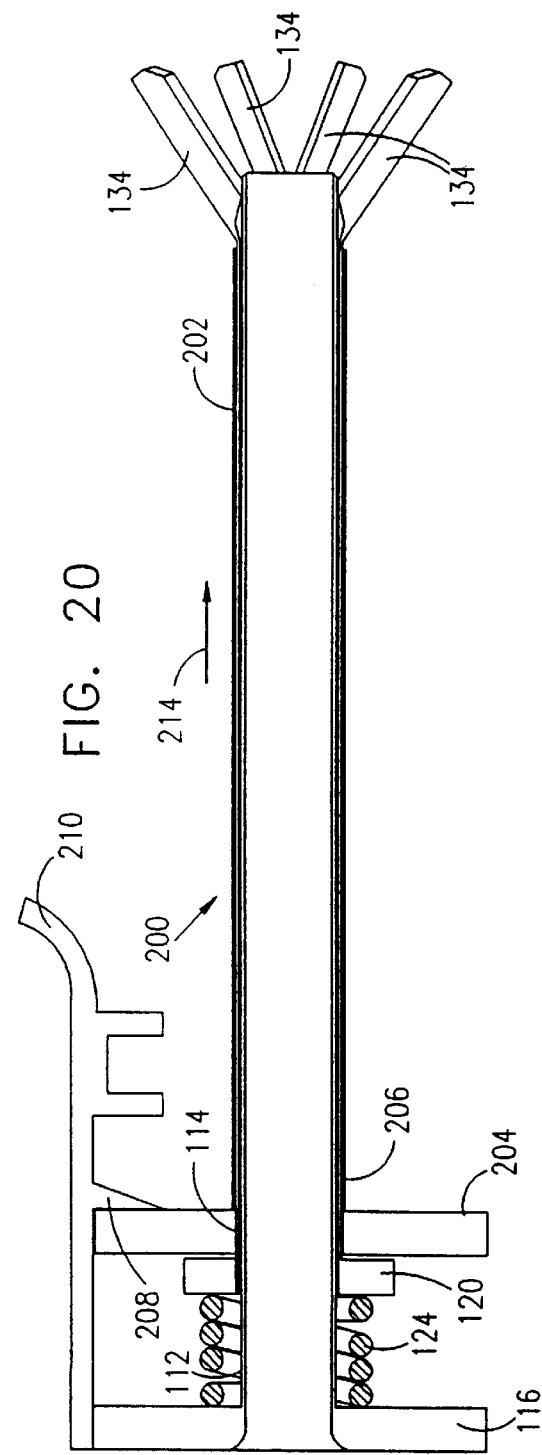

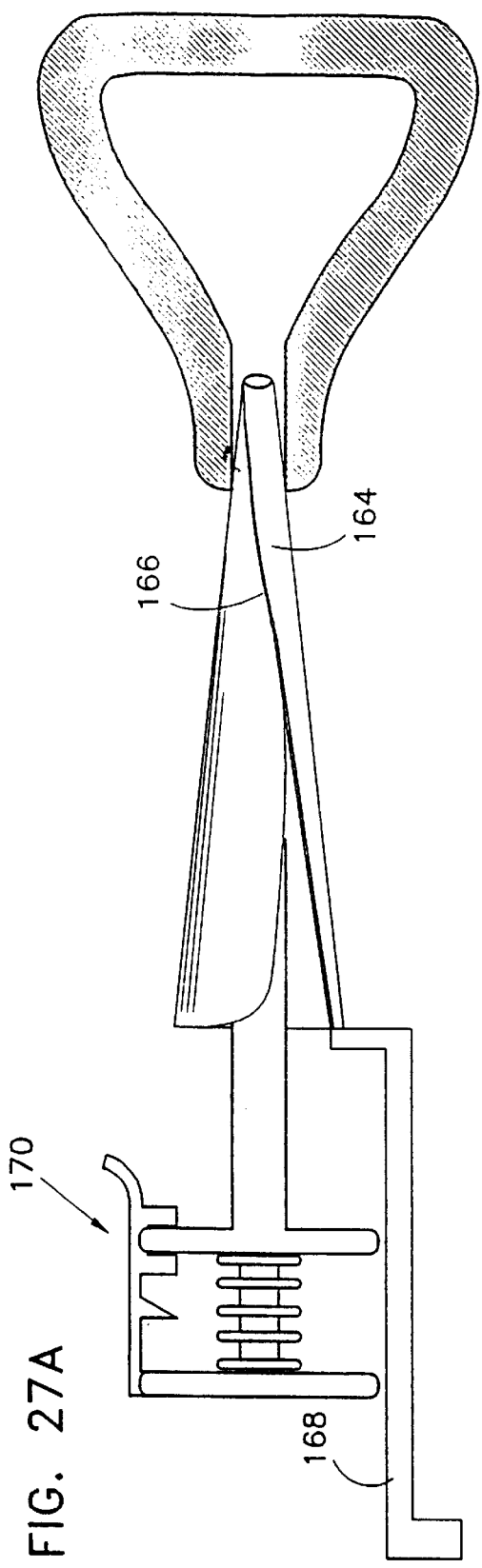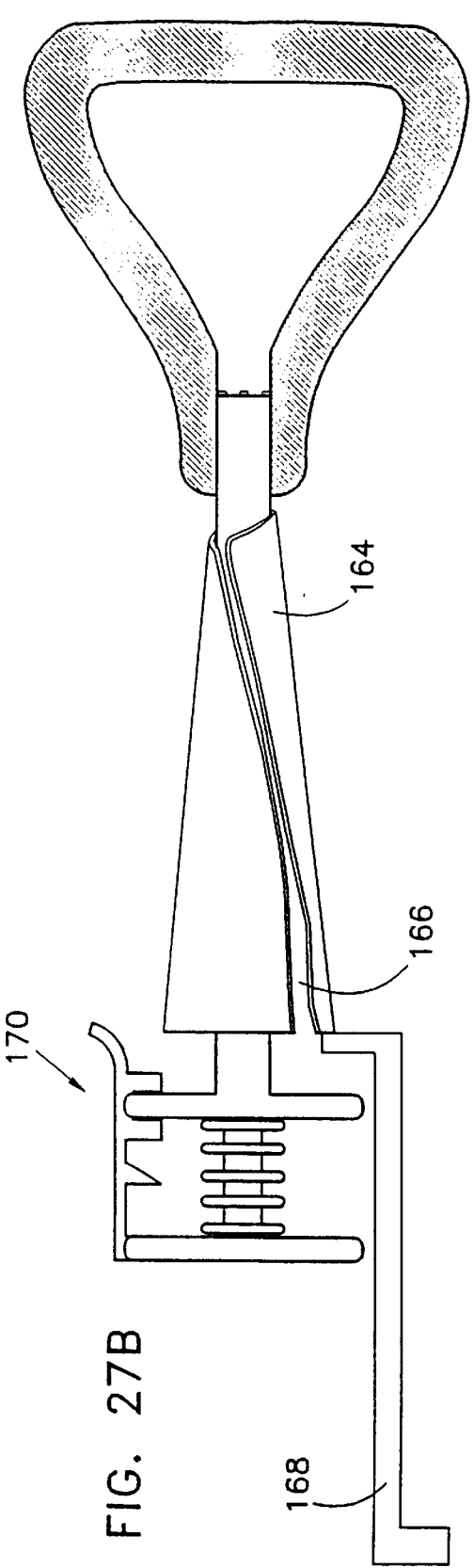

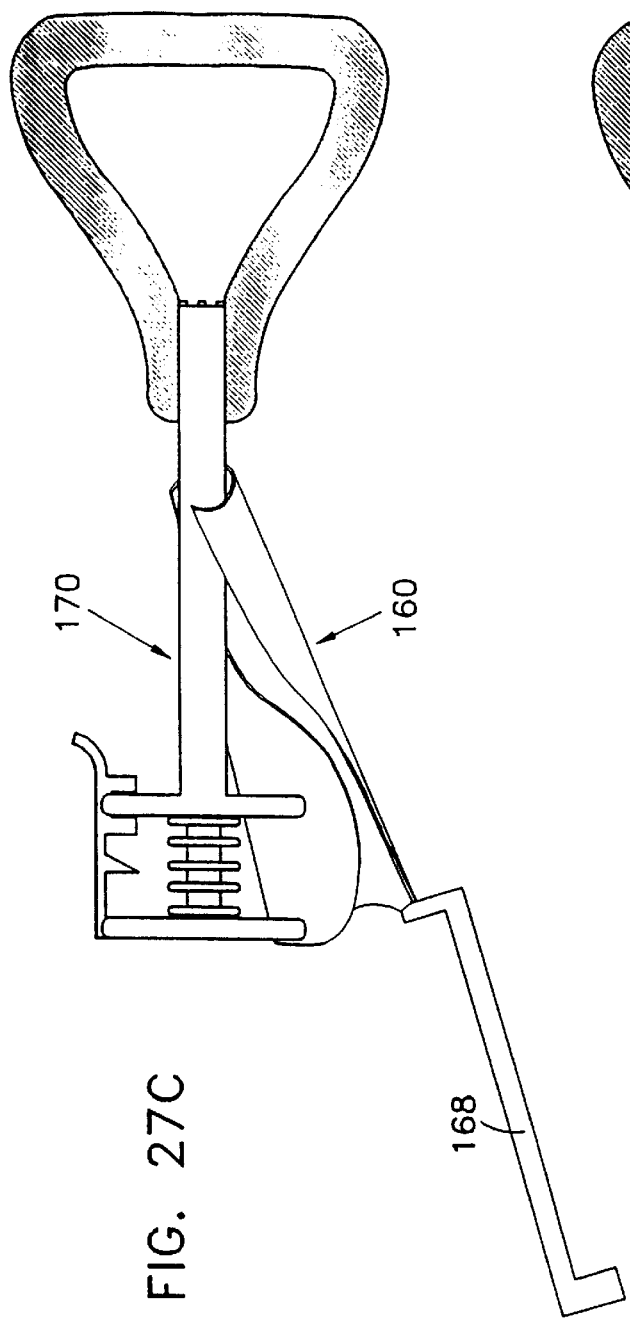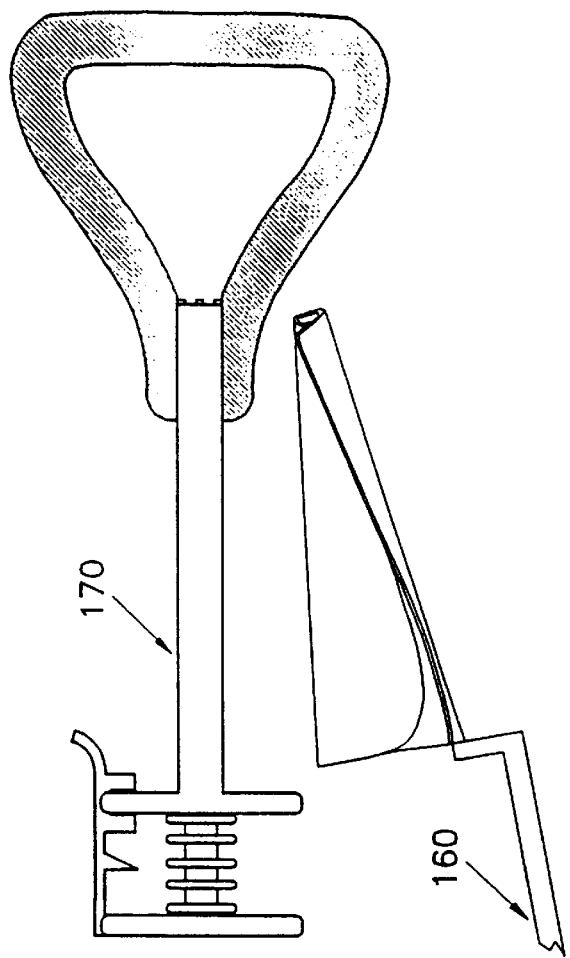

SEIZING INSTRUMENT

The present invention relates to medical instruments generally, and particularly to seizing instruments inserted into body cavities.

In certain medical procedures it is necessary to insert an instrument into a body cavity and seize the inner walls of the cavity. For example, in some gynecological procedures, it is necessary to seize the endocervix while introducing instruments and/or substances through the vagina and the cervix into the uterus. In addition, for some procedures, such as embryo implantations, it is necessary to hold the uterus fixed.

In the prior art, for example, the endocervix is typically seized with a type of sharp pincers called tenaculum.

The present invention seeks to provide a simple seizing instrument for inserting into a body cavity and seizing the inner walls of the cavity.

The present invention is described hereinbelow in detail with reference to preferred embodiments useful in seizing the inner wall of the lower uterine cavity (endocervix). Using the preferred embodiments to seize the endocervix does not require anesthesia and does not endanger the patient or cause pain, discomfort or bleeding thereto. However, it should be emphasized that this is only one example of a possible use for the present invention and is not limiting. The invention is manufacturable in a variety of sizes and shapes, and is readily adaptable for use in the rectum, urethra, esophagus, stomach or other bodily openings, as well as blood vessels.

The present invention comprises a pair of slender tubes, one disposed inside the other. The outside diameter of the pair of tubes is chosen for easy insertion into the particular body cavity, without causing pain thereto or to tissue or sphincters surrounding the opening of the cavity. The insertion end of the tubes is also smoothly tapered and shaped to facilitate insertion.

Once safely inserted, the insertion end of one of the tubes is caused to be deformed generally radially outwards inside the cavity. In one embodiment of the present invention, this is accomplished by making the inner tube from a spring-like material and forming at its insertion end a plurality of axial strips. As long as the inner tube is disposed inside the outer tube, the strips remain constrained together inside the outer tube. After insertion into the body cavity, the outer tube is slid along the inner tube in a direction opposite the insertion direction, thereby exposing the strips of the inner tube and allowing them to spring radially outwards. The instrument can then be used to seize the inner walls of the cavity with the outwardly protruding strips.

In another embodiment of the present invention, the outer tube is formed at one end thereof with stiff axial strips, each formed with a rearwardly facing shoulder. The strips initially touch each other at the tip of the insertion end and do not protrude radially outwards beyond the chosen diameter. This ensures safe insertion into the particular body cavity. The strips may even be weakly joined at their tips to prevent premature opening which could interfere with safe insertion.

The inner tube is slid axially along the outer tube in the insertion direction, thereby butting and pushing against the shoulders. This causes the strips to bend radially outwards. If the tips are weakly joined, the pushing force is sufficient to rupture the joint to allow the strips to bend outwards. The instrument is then used to seize the inner walls of the cavity with the outwardly protruding strips.

In accordance with another preferred embodiment of the present invention, the tubes may be bent or curved towards the insertion end to facilitate insertion into certain cavities. Apertures may be provided at the bent or curved portion of the tubes to allow another path of insertion of devices and/or substances therethrough, in addition to the normal path through the insertion ends of the tubes.

In accordance with yet another preferred embodiment of the present invention, the tubes may be tapered towards the insertion end. The tapering provides the necessary relatively small diameter for insertion into the cavity, while providing a relatively larger diameter opposite to the insertion end which facilitates introduction of instruments and/or materials through the inner tube.

The insertion end of the tapered tubes may be additionally formed with aligned axial slits which allow the tubes to expand radially outwards during insertion of instruments and/or materials, thereby further aiding in the introduction of such instruments and/or materials through the inner tube.

The preferred embodiments of the invention are each provided with handles reversibly attachable to each other. In addition, a safety catch is provided to prevent premature opening of the strips which could hinder safe insertion of the instrument into the body cavity.

The invention may also be adapted to be used in conjunction with fiber optic and/or other devices. Axial apertures may be formed in the tubes for passing therethrough the optic filaments or other devices. Alternatively, or additionally, radial apertures may be formed in the tubes for passing therethrough substances and/or instruments.

In addition, the invention is provided with a slitted funnel guide to further aid safe insertion of the seizing instrument into the body cavity. In a preferred embodiment, the guide is shaped somewhat like a sheet rolled into a cone-shaped funnel and is adapted to receive the insertion end of the seizing instrument. After insertion of the funnel and seizing instrument into the body cavity, the funnel may be pulled transversely against the instrument, thereby unrolling and opening the funnel and allowing it to be slipped off the instrument. The seizing instrument is left inside the cavity where it can be used to seize the inner walls of the cavity as described above.

There is thus provided in accordance with a preferred embodiment of the present invention an instrument for seizing walls of a body cavity including a first portion and a second portion, the second portion being insertable into the cavity and to be reversibly deformable from a first to a second configuration while inside the cavity, the first portion being operative to reversibly deform the second portion from the first to the second configuration, the second portion when in the second configuration being operative to seize the walls of the cavity.

In accordance with a preferred embodiment of the present invention, the first portion of the instrument includes a first end of a pair of inner and outer tubes, the inner tube being disposed inside the outer tube and the outer tube being adapted to slide along the inner tube, and the second portion of the instrument includes a second end of the pair of the inner and the outer tubes, the second end of the inner tube having a plurality of axial slits which define a plurality of axial deformable strips, the strips being deformed radially outwards when the outer tube is slid along the inner tube towards the first end of the inner tube.

Preferably, the material of the strips is resilient and spring-like.

Additionally in accordance with a preferred embodiment of the present invention, each of the plurality of deformable strips is provided with a lip at an end thereof, wherein in the first configuration, the lips do not protrude radially outwards of the outer tube.

Further in accordance with a preferred embodiment of the present invention, the lip is shaped to facilitate insertion into the body cavity.

Preferably the first end of the inner tube is fitted with a first handle and the first end of the outer tube is fitted with a second handle, the first handle being reversibly attachable to the second handle.

Preferably there is provided a safety catch to prevent unintentional axial movement of the inner tube and the outer tube with respect to each other.

In accordance with another preferred embodiment of the present invention, the inner and the outer tubes each have an axial slit extending from their second ends towards their first ends, the axial slits being substantially aligned with each other.

Additionally in accordance with a preferred embodiment of the present invention, the inner and the outer tubes are tapered. In such an embodiment, the inner and the outer tubes may also have aligned axial slits extending from their second ends towards their first ends.

In accordance with another preferred embodiment of the present invention, the first portion of the seizing instrument includes a first end of a pair of inner and outer tubes, the inner tube being disposed inside the outer tube and the outer tube being adapted to slide along the inner tube, and the second portion of the instrument includes a second end of the pair of the inner and the outer tubes, the second end of the outer tube having a plurality of axial slits which define a plurality of axial deformable strips, the strips being deformed radially outwards when the inner tube is slid along the outer tube towards the second end of the outer tube.

Additionally in accordance with a preferred embodiment of the present invention, each deformable strip includes an inner shoulder, such that sliding the inner tube towards the second end of the outer tube causes the second end of the inner tube to butt and push against the shoulder, thereby causing the plurality of strips to deform radially outwards.

Further in accordance with a preferred embodiment of the present invention, the plurality of strips are shaped to facilitate insertion into the body cavity.

In accordance with a preferred embodiment of the present invention, the instrument further includes a safety sleeve which covers at least a portion of the strips in the first configuration and which is retractable to expose the strips in the second configuration.

Additionally in accordance with a preferred embodiment of the present invention, the instrument includes a guiding device which is attached to a distal end of the strips in the first configuration, the guiding device substantially preventing deformation of the plurality of strips radially outwards when in the first configuration, and wherein sliding of the inner tube towards the second end of the outer tube causes detachment of the guiding device from the strips, thereby permitting deformation of the plurality of strips radially outwards, and wherein further sliding of the inner tube towards the second end of the outer tube causes the plurality of strips to deform radially outwards.

The guiding device preferably has a soft tip for guiding the seizing instrument through sharp bends and tight corners.

In accordance with a preferred embodiment of the present invention, the plurality of strips are substantially in contact with one another in the first configuration. In accordance with another preferred embodiment of the present invention, tips of the strips are joined together in the first configuration.

In accordance with a preferred embodiment of the present invention, the seizing instrument includes a device for substantially preventing linear and rotational misalignment of the axial slits.

In accordance with a preferred embodiment of the present invention, the seizing instrument includes a device for substantially preventing linear and rotational misalignment of the first and second tubes with respect to each other.

There is also provided in accordance with a preferred embodiment of the present invention, a slitted funnel guide for guiding insertion of an instrument, comprising a resiliently openable, conical coiled funnel, being adapted to receive an insertable end of the instrument and being retractable transversely from the instrument.

There is also provided in accordance with a preferred embodiment of the present invention, a method for seizing walls of a body cavity comprising the steps of providing an instrument comprising a first portion and a second portion, the second portion being insertable into the cavity and to be reversibly deformable from a first to a second configuration while inside the cavity, the first portion being operative to reversibly deform the second portion from the first to the second configuration, and the second portion when in the second configuration being operative to seize the walls of the cavity, inserting the second portion of the instrument into the cavity, and deforming the second portion into the second configuration and seizing the walls of the cavity.

In accordance with a preferred embodiment of the present invention, the step of inserting further comprises the steps of providing a slitted funnel guide comprising a resiliently openable, conical coiled funnel, inserting the funnel into the cavity, inserting the second portion of the instrument into the funnel, retracting the funnel outwards from the cavity, transversely pulling the funnel against the instrument, thereby causing the coiled funnel to split open and permitting removing the funnel from the instrument, leaving the instrument inside the cavity.

Alternatively, in accordance with another preferred embodiment of the present invention, the step of inserting further comprises the steps of providing a slitted funnel guide comprising a resiliently openable, conical coiled funnel, inserting the funnel and the second portion of the instrument into the cavity, retracting the funnel outwards from the cavity, transversely pulling the funnel against the instrument, thereby causing the coiled funnel to split open and permitting removing the funnel from the instrument, leaving the instrument inside the cavity.

Additionally in accordance with yet another preferred embodiment of the present invention, the step of providing further comprises the step of providing a guiding device for guiding the instrument through non-straight body cavities, the guiding device substantially preventing deformation of the second portion when in the first configuration and being removable so as to permit deformation of the second portion when in the second configuration, and wherein prior to the step of deforming, the guiding device is removed from the second portion to permit deformation of the second portion.

The present invention will be understood and appreciated from the following detailed description, taken in conjunction with the drawings in which:

FIG. 1 is a simplified pictorial illustration of a seizing instrument constructed and operative in accordance with a preferred embodiment of the present invention, the seizing instrument being in a first configuration;

FIG. 2 is a frontal illustration of the seizing instrument of FIG. 1 as viewed along the arrow II in FIG. 1;

FIG. 3 is a sectional illustration of a portion of the seizing instrument of FIG. 1, taken along lines III—III in FIG. 1;

FIG. 7 is a simplified pictorial illustration of a seizing instrument constructed and operative in accordance with another preferred embodiment of the present invention, and wherein the inner and the outer tubes are tapered;

FIG. 8 is a simplified pictorial illustration of the seizing instrument of FIG. 7, and wherein the inner and the outer tubes have aligned axial slits;

FIG. 12 is simplified pictorial illustration of the seizing instrument of FIG. 9 in a second configuration;

FIG. 13 is a frontal illustration of the seizing instrument of FIG. 12 as viewed along the arrow XIII in FIG. 12;

FIG. 14 is a sectional illustration of a portion of the seizing instrument of FIG. 12 taken along lines XIV—XIV in FIG. 12;

FIGS. 18 and 19 are simplified sectional illustrations of a seizing instrument in a first configuration and provided with a retractable safety sleeve, constructed and operative in accordance with a preferred embodiment of the present invention, before and after retraction of the safety sleeve, respectively;

FIG. 20 is a simplified sectional illustration of the seizing instrument of FIGS. 18 and 19 in a second configuration for seizing a cervix;

FIGS. 27A–27D are illustrations of the operation of the funnel guide of FIG. 26.

Figure 4:
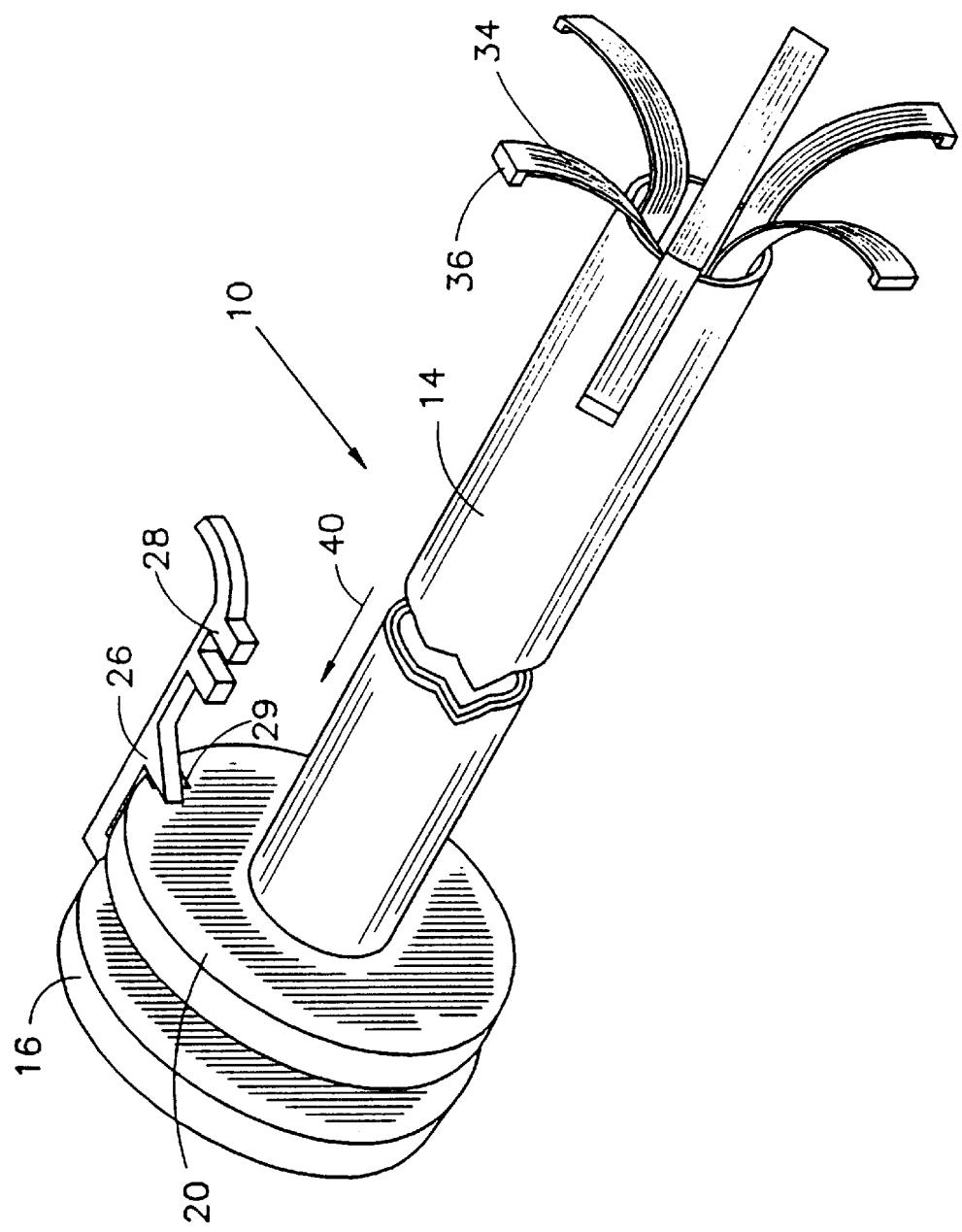
FIG. 4 is simplified pictorial illustration of the seizing instrument of FIG. 1 in a second configuration.

Reference is now made to FIGS. 1–3 which illustrate a seizing instrument 10 constructed and operative in accordance with a preferred embodiment of the present invention. The seizing instrument 10 comprises an inner tube 12 and an outer tube 14, the inner tube 12 being disposed inside the outer tube 14 and the outer tube 14 being adapted to slide along the inner tube 12.

The inner tube 12 preferably has a first handle 16 disposed at a first end 18 thereof. The outer tube 14 preferably has a second handle 20 disposed at a first end 22 thereof. As seen in FIG. 1, the first handle 16 is preferable biased against the second handle 20 with a biasing device, such as a spring 24.

As seen in FIG. 1, the first handle 16 is provided with one or more attachment devices 26, such as hooks, clips or snaps, which may be used to reversibly attach the first handle 16 to the second handle 20. The first handle 16 is also preferably provided with a safety catch 28. The safety catch 28 prevents unintentional axial movement of the first handle 16 and the second handle 20 with respect to each other, and thus also axial movement of the inner tube 12 and the outer tube 14 with respect to each other. The importance of the safety catch 28 is described further hereinbelow.

In accordance with a preferred embodiment of the present invention, seizing instrument 10 has a provision for substantially preventing radial motion of inner tube 12 with respect to outer tube 14. In the embodiment illustrated in FIG. 1, second handle 20 has a groove 29 which is engageable with attachment device 26 and safety catch 28. As long as either attachment device 26 or safety catch 28 is engaged with groove 29, radial motion of second handle 20 and outer tube 14 with respect to first handle 16 and inner tube 12, is substantially prevented. It is appreciated that other devices may be employed to substantially prevent radial motion of the tubes 12 and 14 with respect to each other.

The inner tube 12 has a plurality of axial slits 30 at a second end 32 thereof which define a plurality of axial deformable strips 34. Each strip 34 is preferably provided with a lip 36 which is shaped, such as being rounded, to facilitate insertion of the seizing instrument 10 into a cervix.

The inner tube 12 and the outer tube 14 are preferably made of any durable, medically safe material. The material of the strips 34, or optionally of the entire inner tube 12, further has the property of being resilient and spring-like. The spring-like strips 34 are manufactured such that they protrude radially outwards when not stored inside the outer tube 14.

FIGS. 1–3 illustrate a first configuration of the inner tube 12 and the outer tube 14, in which the strips 34 are held within the outer tube 14. As seen best in FIG. 3, a second end 38 of the outer tube 14 is substantially butted against the lips 36 of the strips 34 in the first configuration. The lips 34 do not protrude radially outwards of the outer tube 14.

Reference is now made to FIG. 4 which illustrates the seizing instrument 10 in a second configuration in which the seizing instrument 10 is operative to seize the cervix. The outer tube 14 is slid along the inner tube 12 in the direction of arrow 40, thereby exposing the strips 34. The spring-like property of the strips 34 causes them return to their manufactured state and deform radially outwards.

It is noted that the safety catch 28 is released from the second handle 20 to allow axial movement of the outer tube 14. As long as the safety catch 28 is attached to the second handle 20, axial movement of the outer tube 14 is prevented and the strips 34 can not prematurely open which could hinder safe insertion into the cervix. The at least one attachment device 26 fastens the first handle 16 to the second handle 20.

Figure 5A:
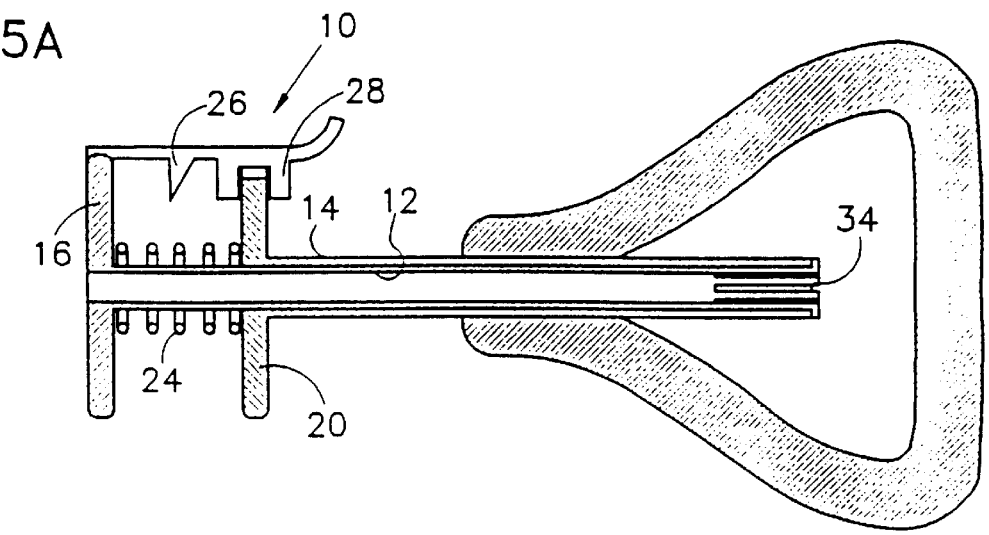
FIG. 5A is a simplified sectional side view of the seizing instrument of FIG. 1 inserted in a cervix and in the first configuration.
Figure 5B:
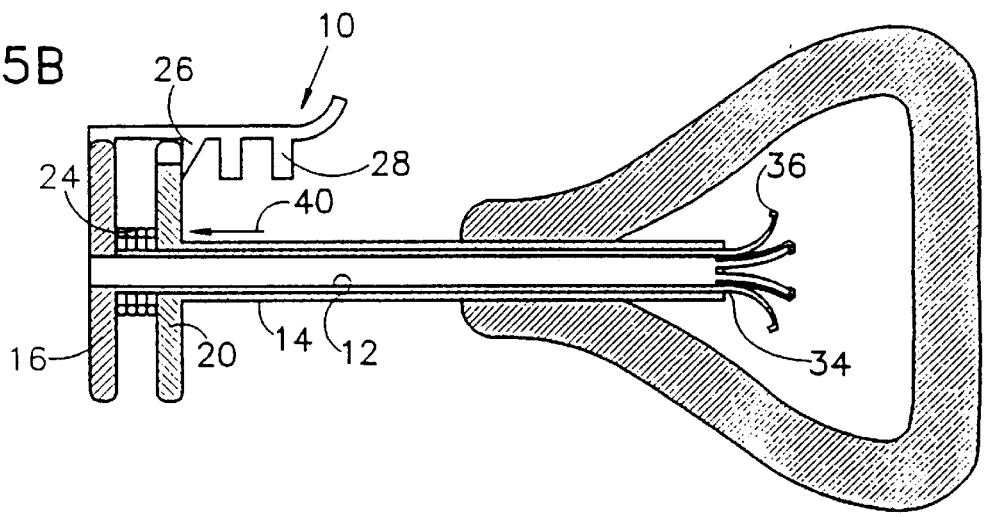
FIG. 5B is a simplified sectional side view of the seizing instrument of FIG. 1 inserted in the cervix and in the second configuration.
Figure 5C:
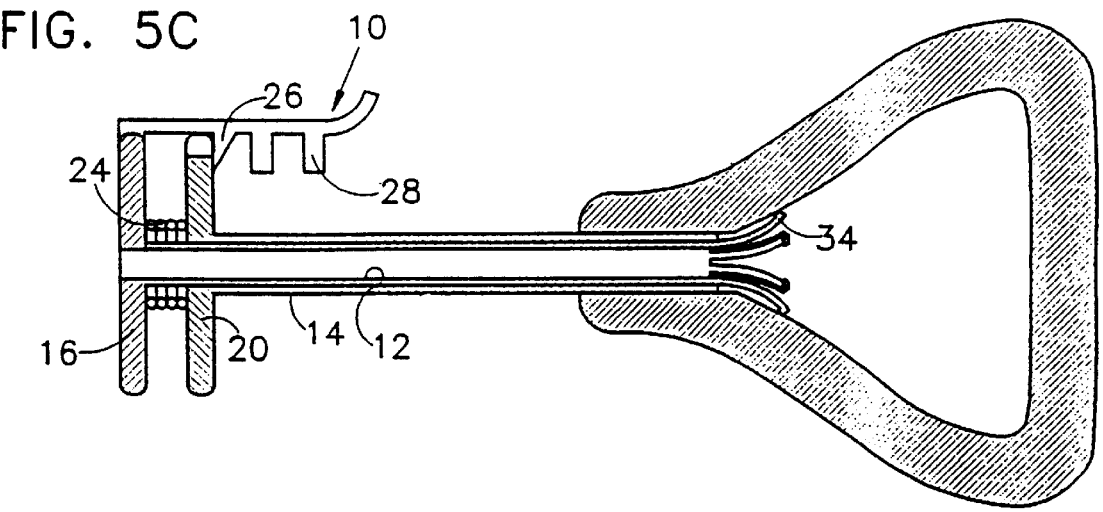
FIG. 5C is a simplified sectional side view of the seizing instrument of FIG. 1 in the second configuration and positioned for seizing the cervix.

Reference is now made to FIGS. 5A–5C which illustrate the operation of the seizing instrument 10. In FIG. 5A, the seizing instrument 10 is inserted into the cervix in the first configuration described hereinabove with reference to FIGS. 1–3.

In FIG. 5B, the outer tube 14 is slid in the direction of arrow 40 along the inner tube 12, thereby exposing the strips 34 which deform radially outwards, and putting the seizing instrument 10 into the second configuration described hereinabove with reference to FIG. 4.

In FIG. 5C, the seizing instrument 10 is pulled against and seizes the cervix.

Figure 6A:
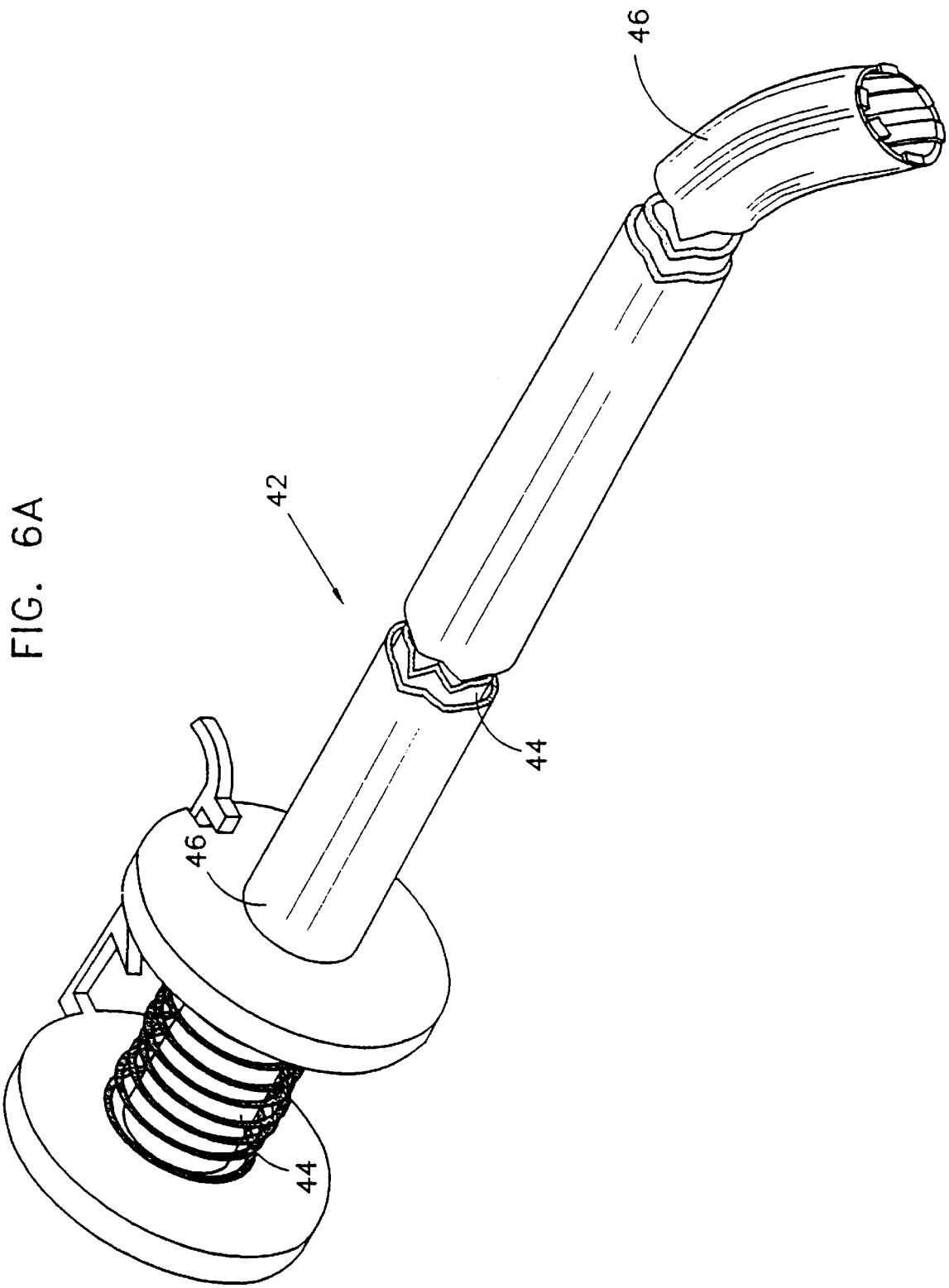
FIG. 6A is a simplified pictorial illustration of a seizing instrument constructed and operative in accordance with another preferred embodiment of the present invention, and wherein the inner and the outer tubes are bent.

The inner tube 12 and the outer tube 14 of the embodiment described hereinabove with reference to FIGS. 1–5C are generally straight along their entire length. Reference is now made to FIG. 6A which illustrates a seizing instrument 42 constructed and operative in accordance with another preferred embodiment of the present invention, and comprising bent inner 44 and outer 46 tubes. Throughout the specification and claims, the term bent includes having a sharp bend or a bend with a radius of curvature. The bending of the tubes may be useful for insertion in certain body cavities.

Figure 6B:
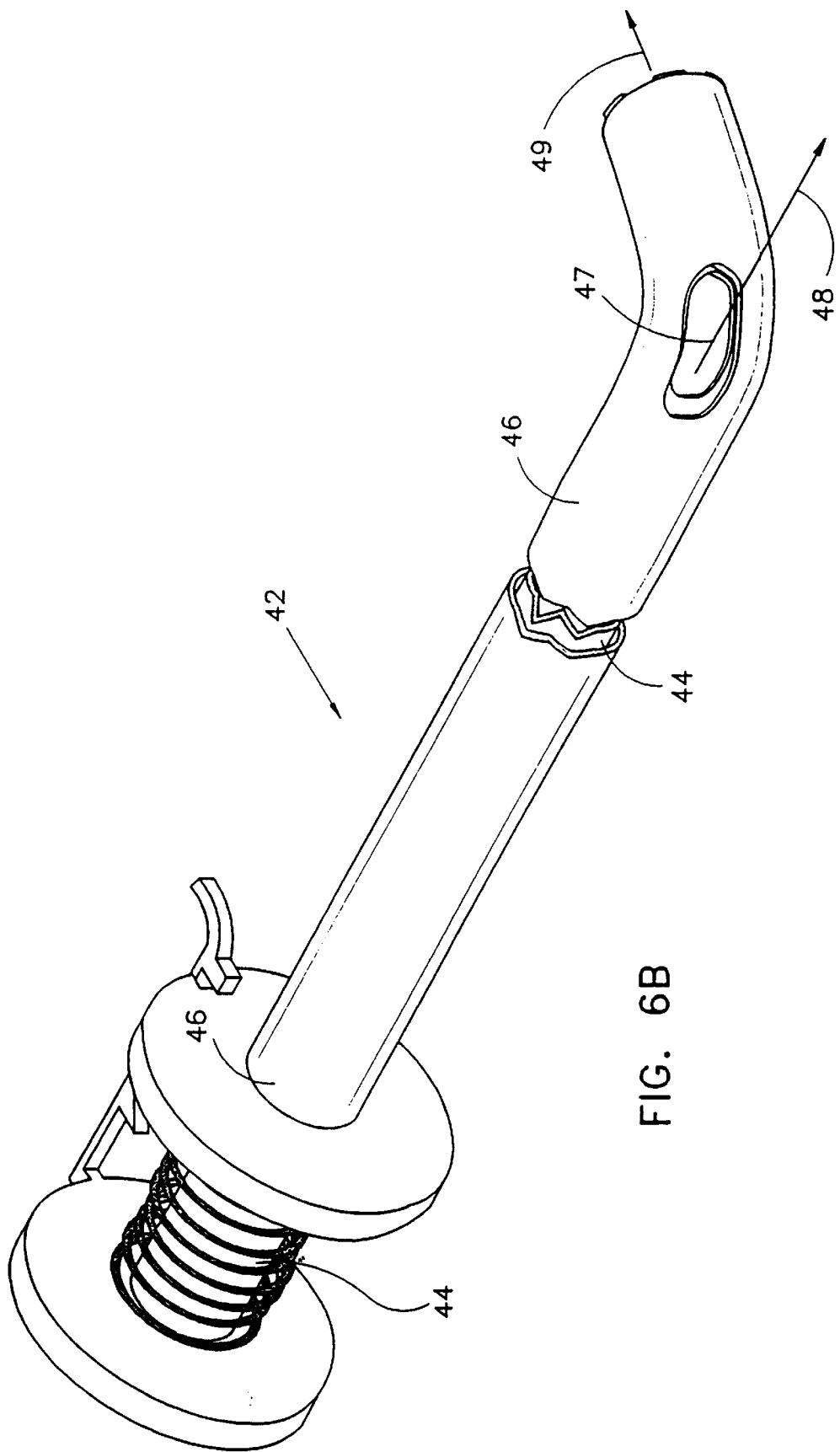
FIG. 6B is a simplified pictorial illustration of a the seizing instrument of FIG. 6A and including radial apertures in the bent portion of the inner and outer tubes.

Referring now to FIG. 6B, it is seen that apertures 47 may be formed in the bent portion of tubes 44 and 46. In this embodiment, devices and/or substances may be introduced into the cervix via apertures 47 in the direction of arrow 48 as well as through the end of tubes 44 and 46 in the direction of arrow 49.

Reference is now made to FIG. 7 which illustrates a seizing instrument 50 constructed and operative in accordance with yet another preferred embodiment of the present invention, and which comprises an inner tube 52 and an outer tube 54 which have a relatively larger diameter at a first end 56 and taper to a relatively smaller diameter at a second end 58. The tapering provides the necessary relatively small diameter for insertion into the cervix, while providing a relatively larger diameter at the first end 56 which facilitates introduction of instruments and/or materials through the inner tube 52.

Reference is now made to FIG. 8 which shows that the inner 52 and the outer 54 tubes of seizing instrument 50, described hereinabove with reference to FIG. 7, may additionally be provided with axial slits 60 and 61 respectively which are substantially aligned with each other. The slits 60 and 61 allow the second ends 58 of the inner 52 and the outer 54 tubes to expand radially outwards during insertion of instruments and/or materials, thereby further aiding in the introduction of such instruments and/or materials through the inner tube 52.

Preferably, seizing instrument 50 is also provided with at least one attachment device 62, a safety catch 64 and a groove 66, which are respectively identical with attachment device 26, safety catch 28 and groove 29 of seizing instrument 10 described hereinabove with reference to FIGS. 1–5C. As long as either attachment device 62 or safety catch 64 is engaged with groove 66, radial motion of outer tube 54 and slit 61 with respect to inner tube 52 and slit 60, is substantially prevented. It is appreciated that other devices may be employed to substantially prevent radial motion of the tubes 52 and 54, as well as slits 60 and 61, with respect to each other.

Figure 10:
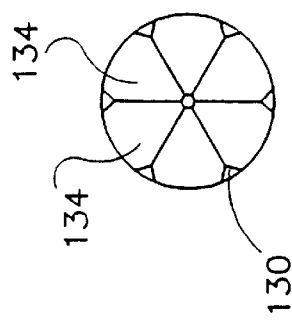
FIG. 10 is a frontal illustration of the seizing instrument of FIG. 9 as viewed along the arrow X in FIG. 9.
Figure 11:
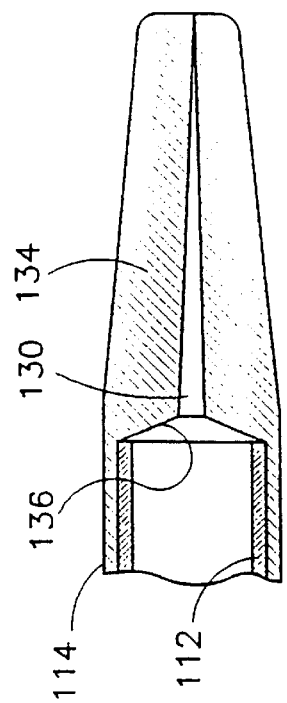
FIG. 11 is a sectional illustration of a portion of the seizing instrument of FIG. 9, taken along lines XI—XI in FIG. 9.
Figure 9:
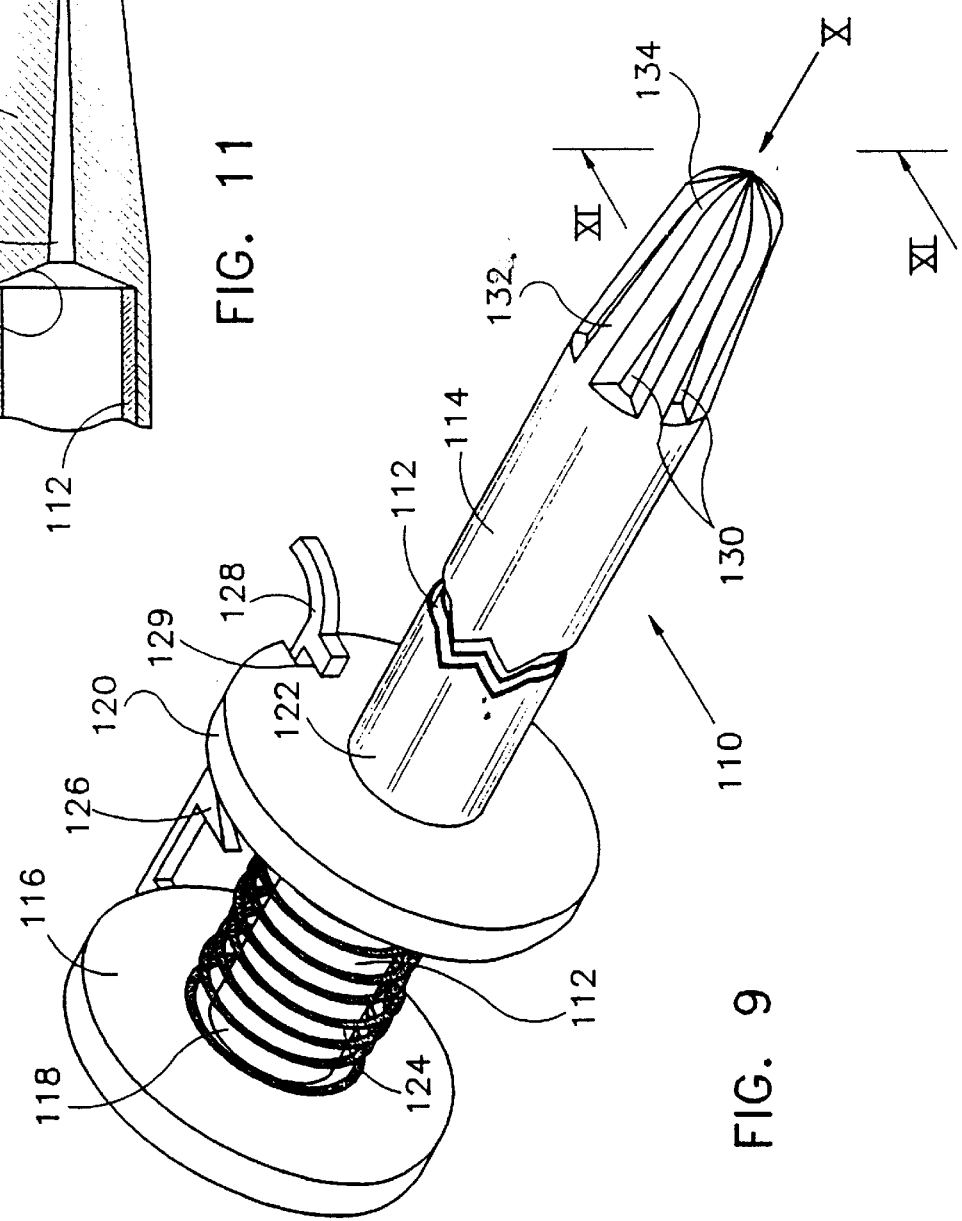
FIG. 9 is a simplified pictorial illustration of a seizing instrument constructed and operative in accordance with another preferred embodiment of the present invention, the seizing instrument being in a first configuration.

Reference is now made to FIGS. 9–11 which illustrate a seizing instrument 110 constructed and operative in accordance with another preferred embodiment of the present invention. The seizing instrument 110 comprises an inner tube 112 and an outer tube 114, the inner tube 112 being disposed inside the outer tube 114 and the outer tube 114 being adapted to slide along the inner tube 112.

The inner tube 112 preferably has a first handle 116 disposed at a first end 118 thereof. The outer tube 114 preferably has a second handle 120 disposed at a first end 122 thereof. As seen in FIG. 9, the first handle 116 is preferable biased against the second handle 120 with a biasing device, such as a spring 124.

As seen in FIG. 9, the first handle 116 is provided with one or more attachment devices 126, such as hooks, clips or snaps, which are operative to reversibly attach the first handle 116 to the second handle 120. The first handle 116 is also preferably provided with a safety catch 128. The safety catch 128 prevents unintentional axial movement of the first handle 116 and the second handle 120 with respect to each other, and thus also axial movement of the inner tube 112 and the outer tube 114 with respect to each other.

In accordance with a preferred embodiment of the present invention, seizing instrument 110 has a provision for substantially preventing radial motion of inner tube 112 with respect to outer tube 114. In the embodiment illustrated in FIG. 9, second handle 120 has a groove 129 which is engageable with attachment device 126 and safety catch 128. As long as either attachment device 126 or safety catch 128 is engaged with groove 129, radial motion of second handle 120 and outer tube 114 with respect to first handle 116 and inner tube 112, is substantially prevented. It is appreciated that other devices may be employed to substantially prevent radial motion of the tubes 112 and 114 with respect to each other.

The outer tube 114 has a plurality of axial slits 130 at a second end 132 thereof which define a plurality of axial deformable strips 134. As seen in FIG. 11, each deformable strip 134 preferably includes an inner shoulder 136. Preferably slits 130 are formed in outer tube 114 with no sharp corners, but rather with rounded corners to prevent stress concentrations, as is known in the art.

FIGS. 9–11 illustrate a first configuration of the inner tube 112 and the outer tube 114. It is noted that the strips 134 are substantially in contact with one another in the first configuration, which is important for safe insertion into the cervix. Optionally, the tips of strips 134 may be weakly joined together, such as by bonding, to ensure that the strips 134 contact one another in the first configuration. This is important to prevent the strips 134 from opening outwards prematurely which could interfere with safe insertion of the seizing instrument 110 into the cervix.

Reference is now made to FIGS. 12–14 which illustrate the operation of the seizing instrument 110. As shown in FIG. 12, the inner tube 112 is slid along the inside of the outer tube 114 in the direction of arrow 140, such that an end 142 of the inner tube 112 butts against the inner shoulders 136 of the strips 134 of the outer tube 114. Further sliding of the inner tube 112 in the direction of the arrow 140 causes the end 142 to push against the shoulders 136, thereby causing the plurality of strips 134 to deform radially outwards as shown pictorially in FIG. 13 and in section in FIG. 14. If the tips of the strips 134 are weakly joined, the pushing force is sufficient to rupture the joint to allow the strips 134 to bend outwards. The seizing instrument 110 is then used to seize the cervical walls with the outwardly protruding strips 134.

It is appreciated that seizing instrument 110 may be provided with a bend with apertures, may be tapered and/or may be provided with axial slits as described hereinabove for seizing instrument 10 with reference to FIGS. 6B, 7 and 8.

Figure 15:
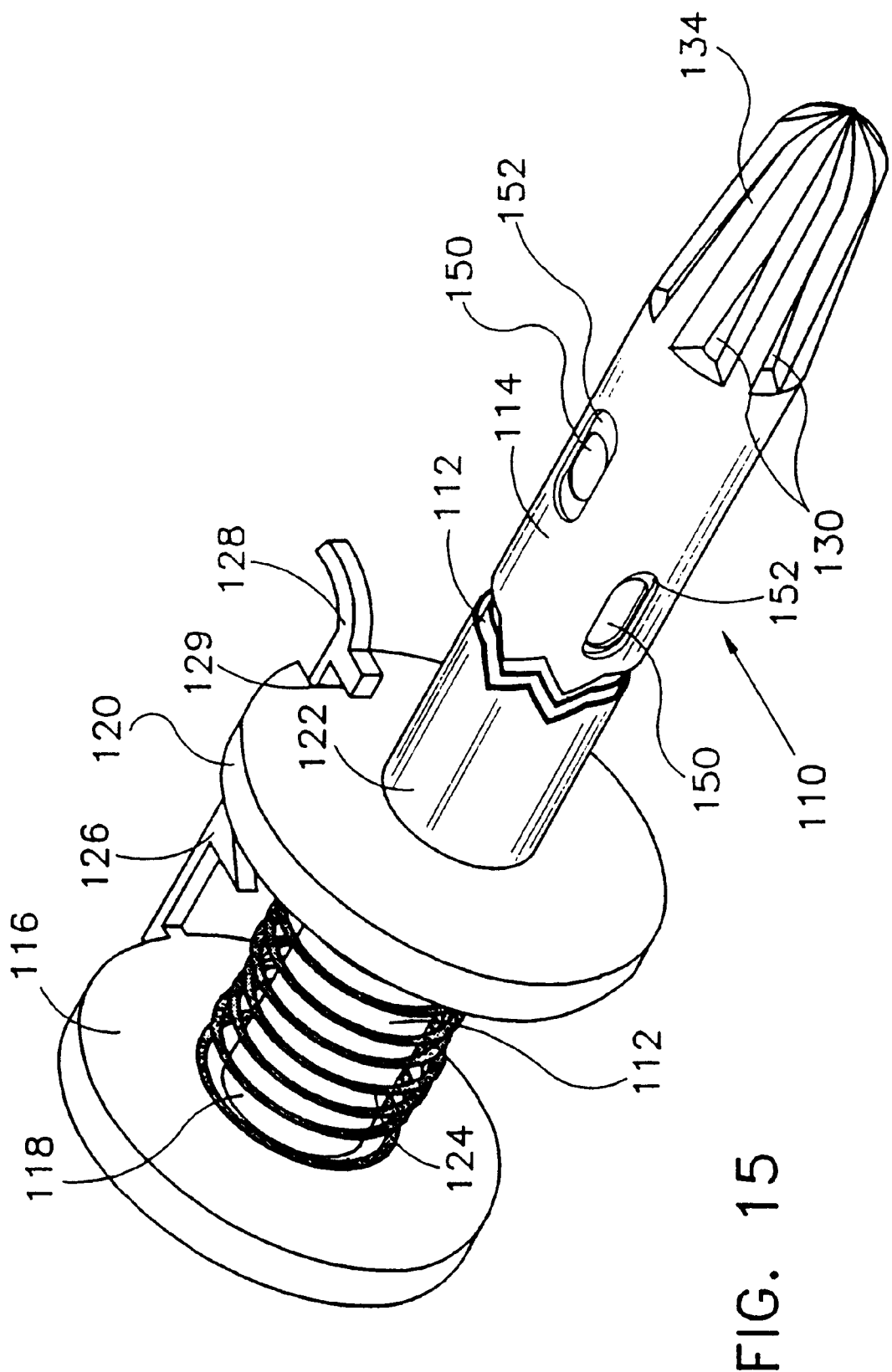
FIG. 15 is a simplified pictorial illustration of a seizing instrument provided with radial apertures constructed and operative in accordance with a preferred embodiment of the present invention.

Reference is now made to FIG. 15 which illustrates seizing instrument 110 provided with substantially aligned radial apertures 150 and 152 formed in the inner 112 and the outer 114 tubes respectively. Apertures 150 and 152 may be used to pass therethrough instruments and/or substances into the cervix.

Figure 16:
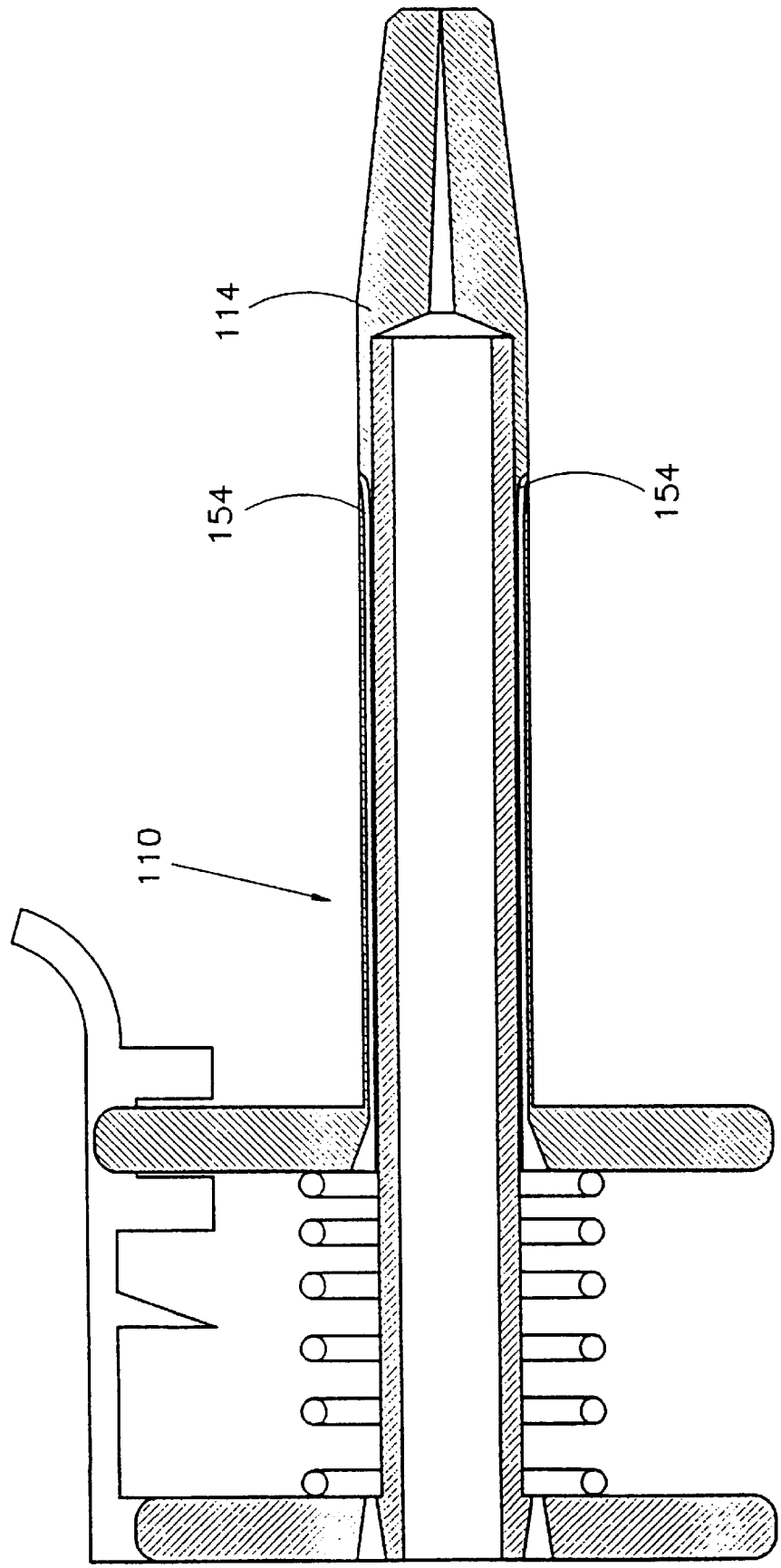
FIG. 16 is a simplified sectional illustration of a seizing instrument provided with axial apertures constructed and operative in accordance with a preferred embodiment of the present invention.

Reference is now made to FIG. 16 which shows that alternatively, or additionally, axial apertures 154 may be formed in the outer tube 114 for passing therethrough devices, such as fiber optic and/or other devices. Apertures 154 are shown in section in FIG. 16. It is appreciated that radial and axial apertures may be formed in seizing instrument 10 as well.

Figure 17:
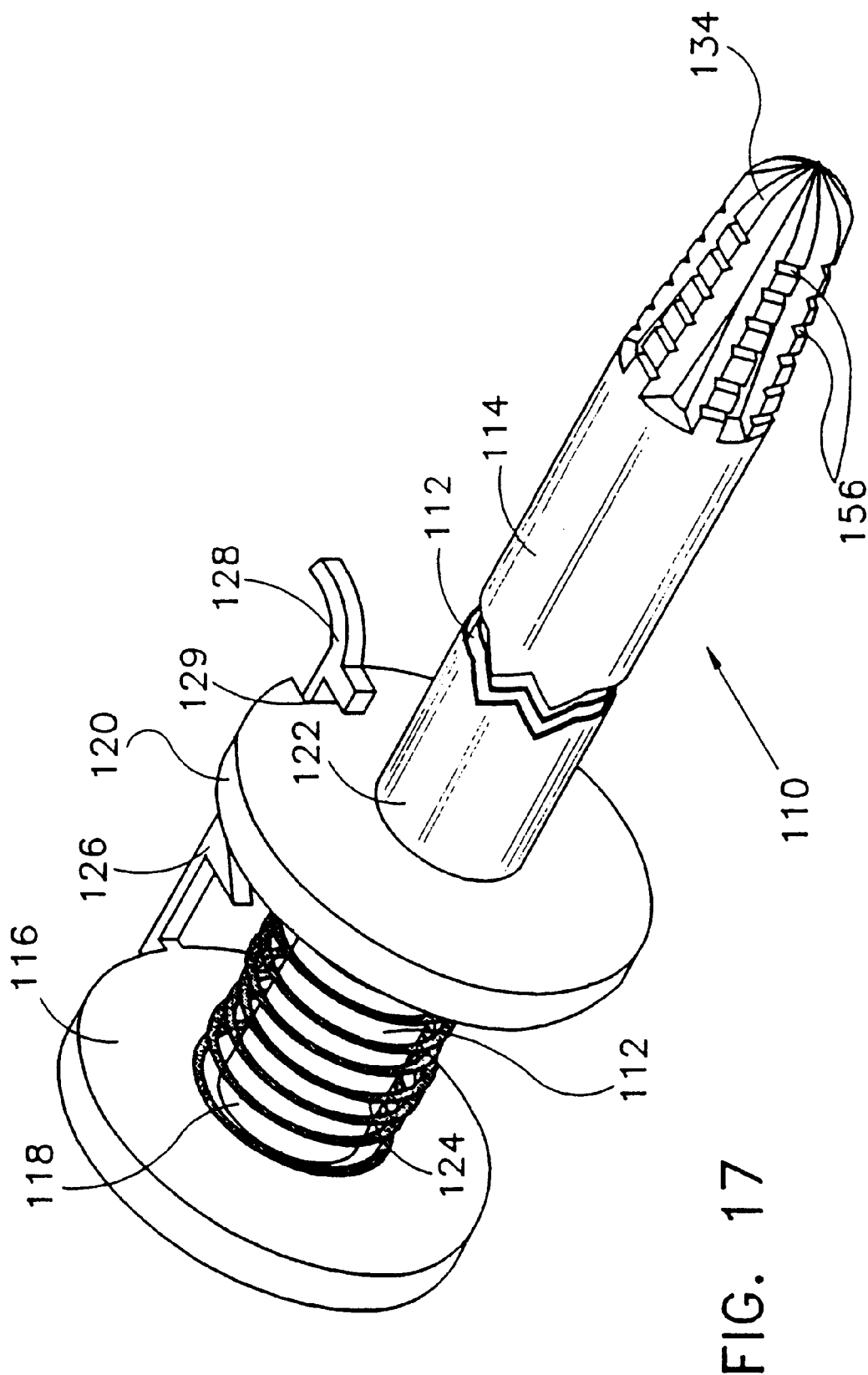
FIG. 17 is a simplified pictorial illustration of a seizing instrument provided with roughened strips constructed and operative in accordance with a preferred embodiment of the present invention.

Reference is now made to FIG. 17 which illustrates seizing instrument 110 with an outer surface of strips 134 roughened such as by forming grooves 156 thereon. Roughening may help in seizing certain tissues.

Reference is now made to FIGS. 18–22 which illustrate a seizing instrument 200, constructed and operative in accordance with still another preferred embodiment of the present invention.

Figure 18:
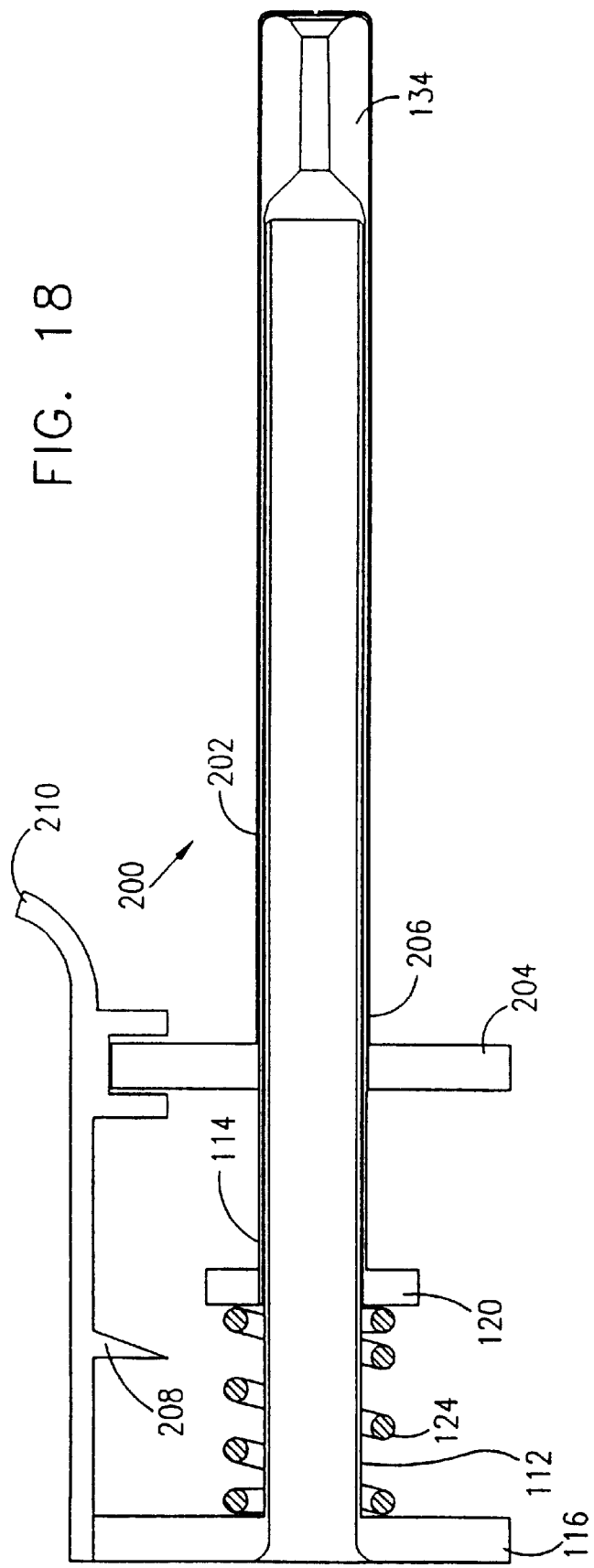
Figure 21:
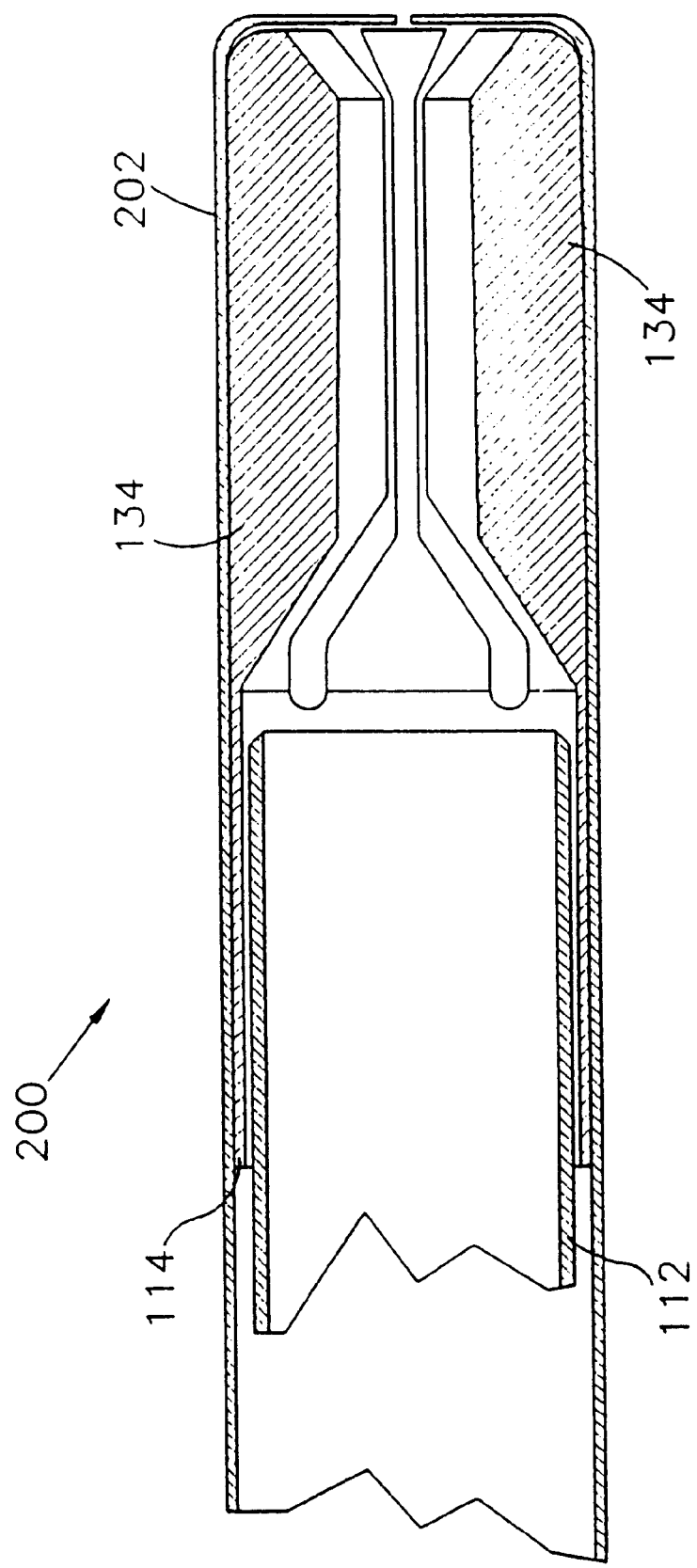
FIGS. 21 and 22 are enlarged illustrations of a portion of the seizing instrument shown in FIGS. 18 and 20, respectively.

Seizing instrument 200 is preferably constructed substantially similarly to seizing instrument 110 described hereinabove, with like numerals designating like elements. Seizing instrument 200 is preferably provided with a retractable safety sleeve 202 which initially substantially covers and envelops deformable strips 134, as seen in FIGS. 18 and 21. Safety sleeve 202 is preferably constructed of a thin pliable material, such as a thin plastic sheet fashioned to closely fit over outer tube 114 and deformable strips 134. A third handle 204 (FIG. 18) is preferably attached to a proximal end 206 of safety sleeve 202.

As seen in FIG. 18, first handle 116 may be provided with one or more attachment devices 208, such as hooks, clips or snaps, which may be used to reversibly attach first handle 116 to third handle 204. It is noted that second handle 120 is shown to be of smaller size than first handle 116 and third handle 204, however, second handle 120 may be any other convenient size. A safety catch 210 may also be provided which prevents unintentional axial movement of first handle 116 and third handle 204 with respect to each other.

As seen in FIG. 19, by retracting third handle 204 generally in the direction of an arrow 212, retractable safety sleeve 202 is pulled towards its proximal end 206, thereby exposing deformable strips 134.

Figure 22:
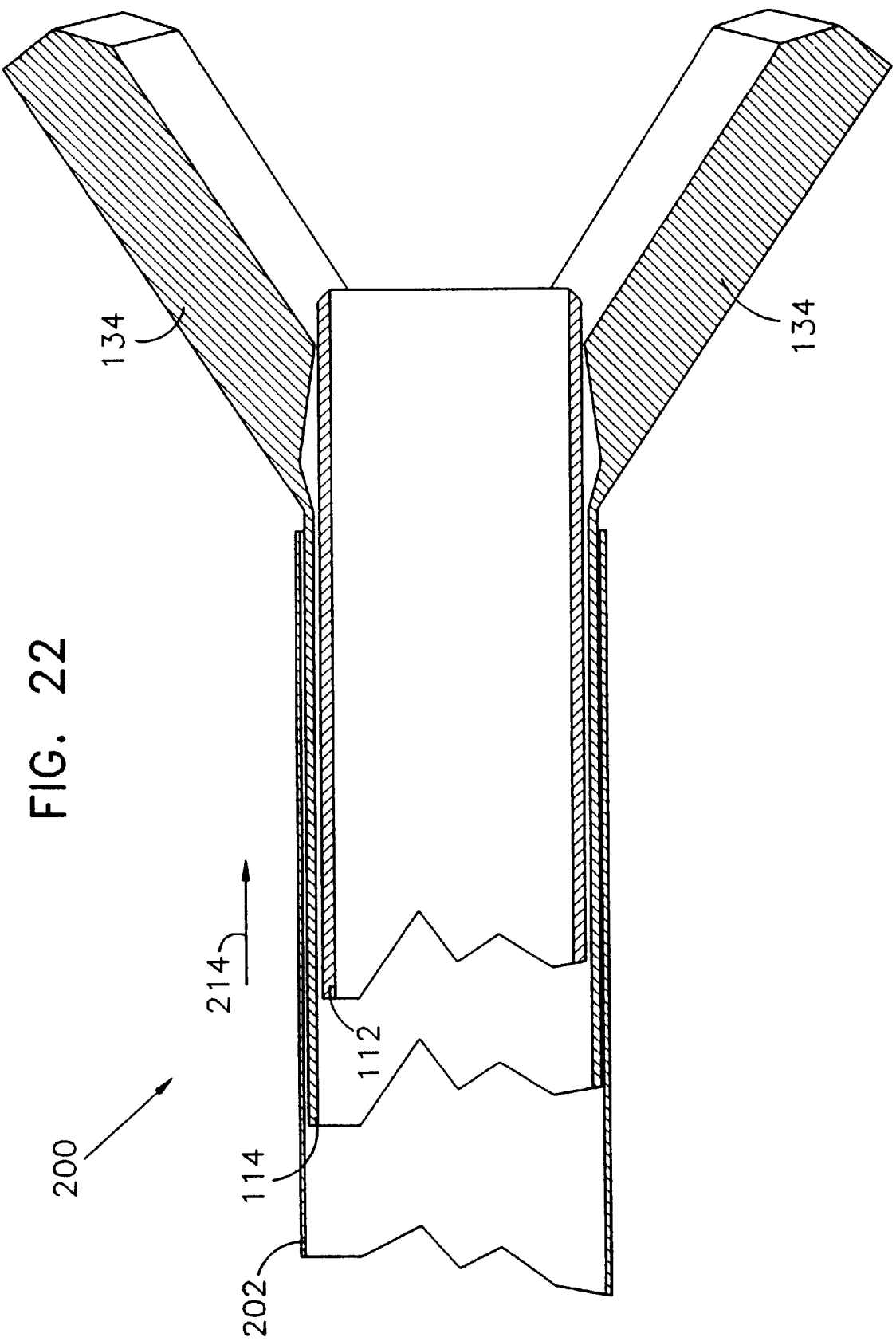

As seen in FIGS. 20 and 22, by pushing first handle 116 generally in the direction of an arrow 214, the plurality of strips 134 are deformed radially outwards and are in a position to seize the inner walls of a body cavity (not shown).

Figure 23:
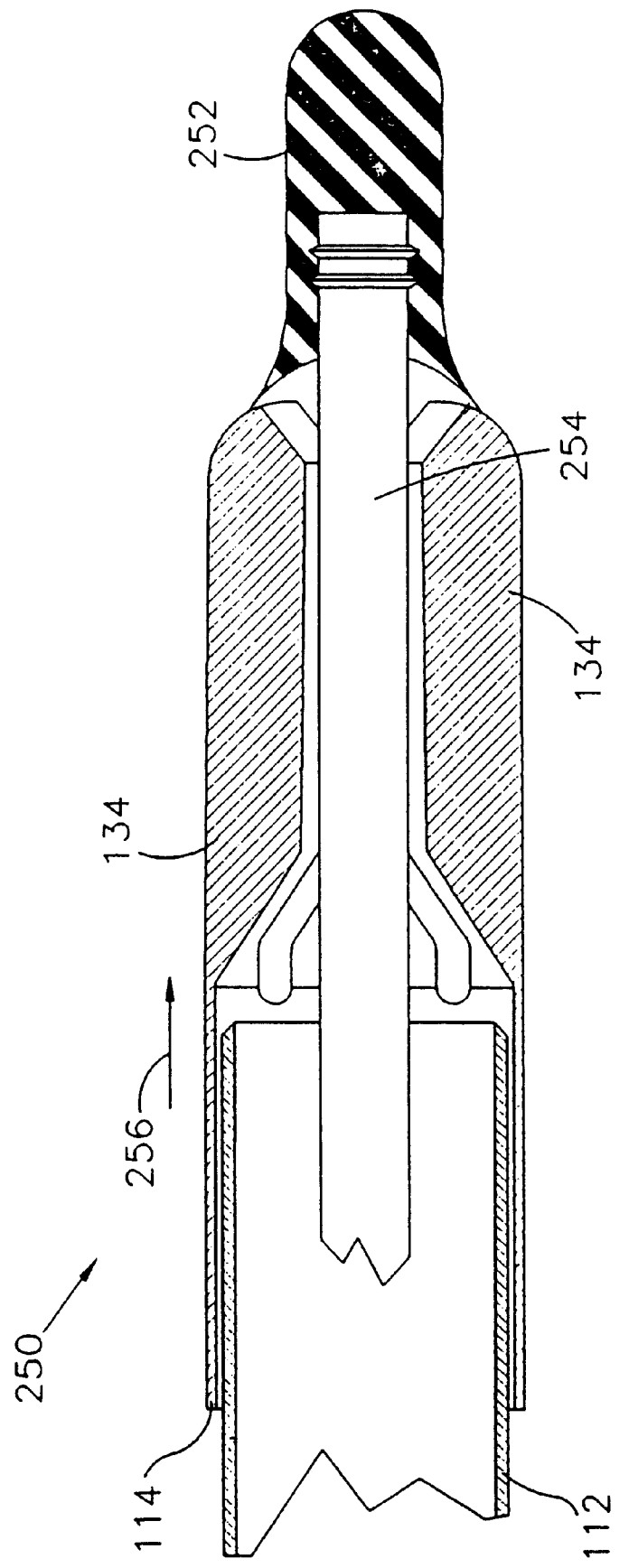
FIGS. 23 and 24 are simplified sectional illustrations of a seizing instrument in a first configuration and provided with a guiding device, constructed and operative in accordance with a preferred embodiment of the present invention, before and after removal of the guiding device, respectively.
Figure 24:
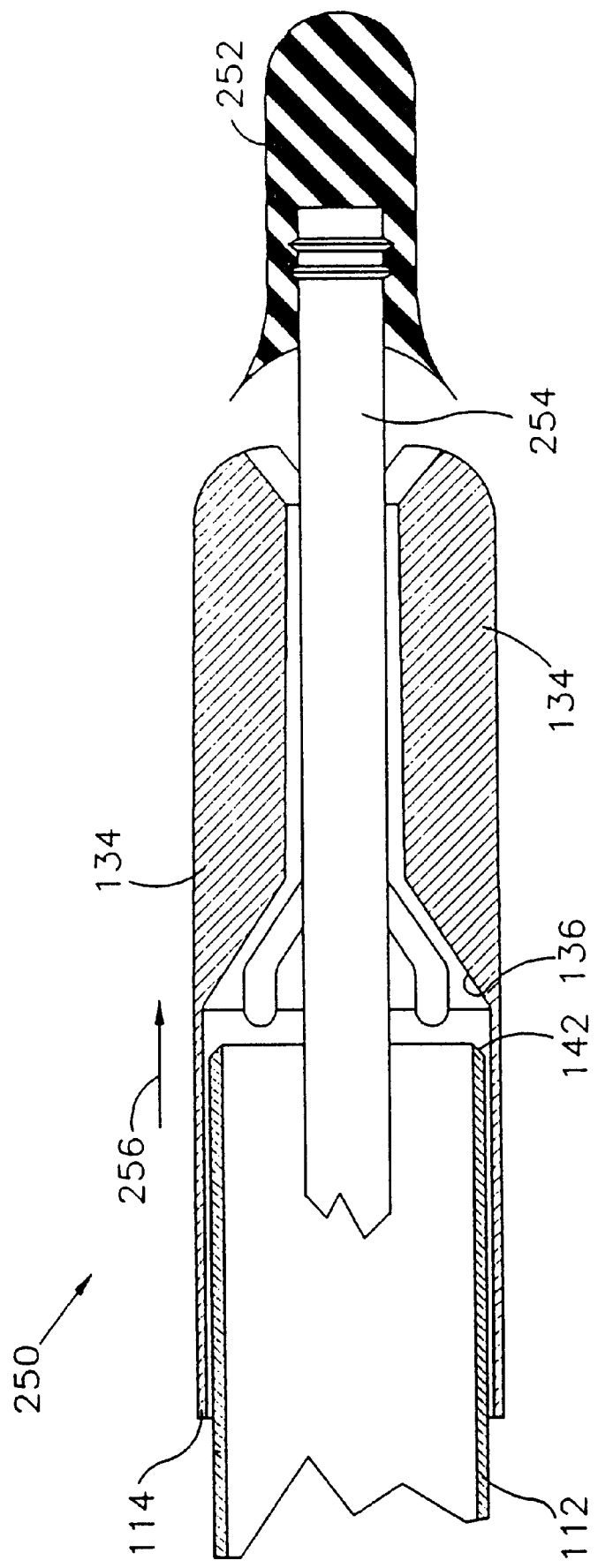
Figure 25:
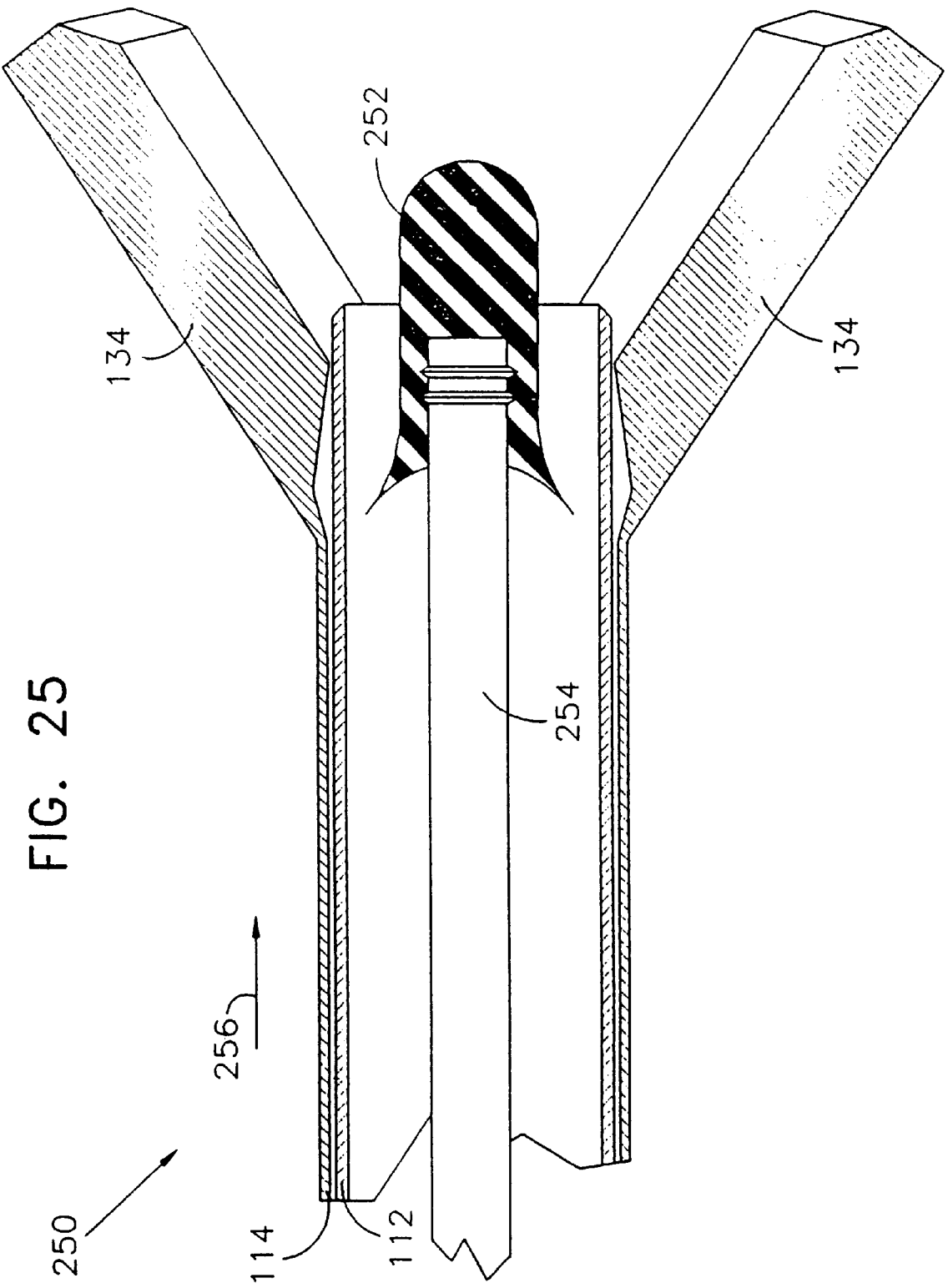
FIG. 25 is a simplified sectional illustration of the seizing instrument of FIGS. 23 and 24 in a second configuration for seizing a cervix.

Reference is now made to FIGS. 23–25 which illustrate a seizing instrument 250 with a guiding device 252, constructed and operative in accordance with a preferred embodiment of the present invention. Seizing instrument 250 is preferably constructed substantially similarly to seizing instrument 110 described hereinabove, with like numerals designating like elements.

Guiding device 252 is preferably constructed of a soft, resilient and flexible material, such as a soft rubber, so as to facilitate the insertion of seizing instrument 250 into a body cavity (not shown), such as through sharp bends and tight corners. Guiding device 252 may have any suitable shape for facilitating entrance into a body cavity. Guiding device 252 is preferably fixedly attached to a rod 254 which passes through the first and second handles (not shown) of seizing instrument 250. In FIG. 23, guiding device 252 initially butts against a distal end of deformable strips 134, thereby substantially preventing deformation of strips 134 radially outwards.

Reference is now made to FIG. 24. By pushing rod 254 generally in the direction of an arrow 256, guiding device 252 is pushed away from strips 134, thereby permitting subsequent deformation of the strips 134.

Reference is now made to FIG. 25. Sliding inner tube 112 generally in the direction of arrow 256 causes strips 134 to deform radially outwards, thereby bringing seizing instrument 250 into a configuration for seizing a cervix or other body cavity. Once strips 134 have been deformed, rod 254 may be used to retract guiding device 252 through seizing instrument 250. Guiding device 252 may then be disposed of, or may be sterilized for further use.

Figure 26:
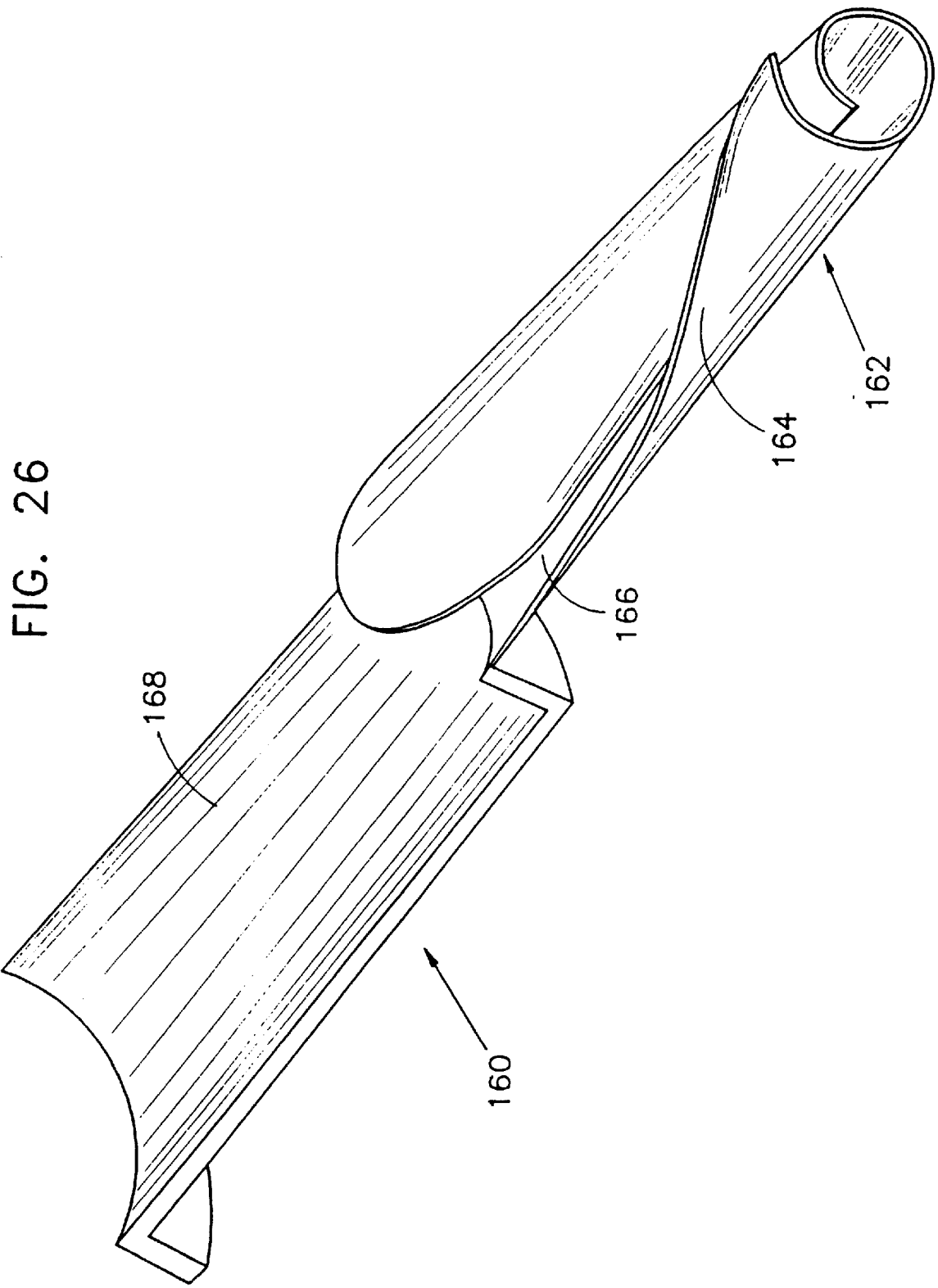
FIG. 26 is a simplified pictorial illustration of a slitted funnel guide constructed and operative in accordance with a preferred embodiment of the present invention.

Reference is now made to FIG. 26 which illustrates a slitted funnel guide 160 constructed and operative in accordance with a preferred embodiment of the present invention. Guide 160 is constructed of resilient material and comprises an insertion portion 162 which is shaped somewhat like a sheet rolled into a cone-shaped funnel 164 with a generally axial slit 166. Funnel 164 is adapted to receive the insertion end of any seizing instrument, such as instrument 10 or 110, constructed and operative in accordance with a preferred embodiment of the present invention.

Guide 160 preferably further comprises a handle 168.

Reference is now made to FIGS. 27A–27D which illustrate the operation of the funnel guide 160. As seen in FIG. 27A, a user inserts the funnel guide 160 into the cervix. Since the funnel 164 tapers outwards from the cervix, a seizing instrument 170 is easily inserted through the funnel guide 160 into the cervix, as seen in FIG. 27B. Alternatively, seizing instrument 170 may be inserted together with funnel guide 160 into the cervix.

Once the instrument 170 is inserted in the cervix, the funnel guide 160 may be pulled outwards from the cervix. The slit 166 of the funnel 164 widens as the funnel 164 is pulled back somewhat transversely to the instrument 170, as seen in FIG. 27C. This allows the funnel guide 160 to slip off the instrument 170 and leaves the instrument 170 inside the cervix, as seen in FIG. 27D. Instrument 170 can then be used to seize the endocervix as described above for seizing instrument 10 or 110.

It will be appreciated by persons skilled in the art that the present invention is not limited to what has been particularly shown and described hereinabove. Rather, the scope of the present invention is defined only by the claims that follow:

I claim:

1. An instrument for seizing walls of a body cavity comprising:
   a first portion and a second portion, said second portion being insertable into said cavity and to be reversibly deformable from a first to a second configuration while inside said cavity, said first portion being operative to reversibly deform said second portion from said first to said second configuration, said second portion when in said second configuration being operative to seize said walls of said cavity; wherein said first portion of said seizing instrument comprises a first end of a pair of inner and outer tubes, said inner tube being disposed inside said outer tube and said outer tube being adapted to slide along said inner tube, and said second portion of said instrument comprises a second end of said pair of said inner and said outer tubes, said second end of said outer tube having a plurality of axial slits which define a plurality of axial deformable strips, said strips being deformed radially outwards when said inner tube is slid along said outer tube towards said second end of said outer tube; wherein said plurality of strips are shaped to facilitate insertion into said body cavity; and a safety sleeve which covers at least a portion of said strips in said first configuration and which is retractable to expose said strips in said second configuration.

2. An instrument for seizing walls of a body cavity comprising:

a first portion and a second portion, said second portion being insertable into said cavity and to be reversibly deformable from a first to a second configuration while inside said cavity, said first portion being operative to reversibly deform said second portion from said first to said second configuration, said second portion when in said second configuration being operative to seize said walls of said cavity; wherein said first portion of said seizing instrument comprises a first end of a pair of inner and outer tubes, said inner tube being disposed inside said outer tube and said outer tube being adapted to slide along said inner tube, and said second portion of said instrument comprises a second end of said pair of said inner and said outer tubes, said second end of said outer tube having a plurality of axial slits which define a plurality of axial deformable strips, said strips being deformed radially outwards when said inner tube is slid along said outer tube towards said second end of said outer tube; wherein said plurality of strips are shaped to facilitate insertion into said body cavity;

wherein said plurality of strips are rupturably joined together in said first configuration.

3. An instrument according to claim 2 and wherein an outer surface of said strips is roughened.

4. An instrument for seizing walls of a body cavity comprising:

a first portion and a second portion, said second portion being insertable into said cavity and to be reversibly deformable from a first to a second configuration while inside said cavity, said first portion being operative to reversibly deform said second portion from said first to said second configuration, said second portion when in said second configuration being operative to seize said walls of said cavity;

wherein said first portion of said instrument comprises a first end of a pair of inner and outer tubes, said inner tube being disposed inside said outer tube and said outer tube being adapted to slide along said inner tube, and said second portion of said instrument comprises a second end of said pair of said inner and said outer tubes, said second end of said inner tube having a plurality of axial slits which define a plurality of axial deformable strips, said strips being deformed radially outwards when said outer tube is slid along said inner tube towards said first end of said inner tube;

wherein said inner and said outer tubes are each provided with a bend towards their second ends.

5. An instrument according to claim 4 and wherein said bends each have an aperture.

6. An instrument for seizing walls of a body cavity comprising:

a first portion and a second portion, said second portion being insertable into said cavity and to be reversibly deformable from a first to a second configuration while inside said cavity, said first portion being operative to reversibly deform said second portion from said first to said second configuration, said second portion when in said second configuration being operative to seize said walls of said cavity;

wherein said first portion of said instrument comprises a first end of a pair of inner and outer tubes, said inner tube being disposed inside said outer tube and said outer tube being adapted to slide along said inner tube, and said second portion of said instrument comprises a second end of said pair of said inner and said outer tubes, said second end of said inner tube having a plurality of axial slits which define a plurality of axial deformable strips, said strips being deformed radially outwards when said outer tube is slid along said inner tube towards said first end of said inner tube;

wherein said inner and said outer tubes each have an axial slit extending from their second ends towards their first ends, said axial slits being substantially aligned with each other.

7. An instrument according to claim 6 and comprising a device for substantially preventing linear and rotational misalignment of said axial slits.

8. An instrument for seizing walls of a body cavity comprising:

a first portion and a second portion, said second portion being insertable into said cavity and to be reversibly deformable from a first to a second configuration while inside said cavity, said first portion being operative to reversibly deform said second portion from said first to said second configuration, said second portion when in said second configuration being operative to seize said walls of said cavity; and a slitted funnel guide for guiding insertion of said instrument, said funnel guide being constructed of a resilient sheet rolled into a cone-shaped funnel with a generally axial slit formed therein, said cone-shaped funnel defining an insertion portion adapted to receive therein an insertable end of said instrument.

9. A method for seizing walls of a body cavity comprising the steps of:

providing an instrument comprising a first portion and a second portion, said second portion being insertable into said cavity and to be reversibly deformable from a first to a second configuration while inside said cavity, said first portion being operative to reversibly deform said second portion from said first to said second configuration, and said second portion when in said second configuration being operative to seize said walls of said cavity;

inserting said second portion of said instrument into said cavity; and deforming said second portion into said second configuration and seizing said walls of said cavity;

wherein the step of inserting further comprises the steps of:

providing a slitted funnel guide comprising a resiliently openable, conical coiled funnel;

inserting said funnel into said cavity;

inserting said second portion of said instrument into said funnel;

retracting said funnel outwards from said cavity;

transversely pulling said funnel against said instrument, thereby causing said coiled funnel to split open and permitting removing said funnel from said instrument, leaving said instrument inside said cavity.

10. A method for seizing walls of a body cavity comprising the steps of:

providing an instrument comprising a first portion and a second portion, said second portion being insertable into said cavity and to be reversibly deformable from a first to a second configuration while inside said cavity, said first portion being operative to reversibly deform said second portion from said first to said second configuration, and said second portion when in said second configuration being operative to seize said walls of said cavity;

inserting said second portion of said instrument into said cavity; and deforming said second portion into said second configuration and seizing said walls of said cavity;

wherein the step of inserting further comprises the steps of:

providing a slitted funnel guide comprising a resiliently openable, conical coiled funnel;

inserting said funnel and said second portion of said instrument into cavity;

retracting said funnel outwards from said cavity;

transversely pulling said funnel against said instrument, thereby causing said coiled funnel to split open and permitting removing said funnel from said instrument, leaving said instrument inside said cavity.

11. A method for seizing walls of a body cavity comprising the steps of:

providing an instrument comprising a first portion and a second portion, said second portion being insertable into said cavity and to be reversibly deformable from a first to a second configuration while inside said cavity, said first portion being operative to reversibly deform said second portion from said first to said second configuration, and said second portion when in said second configuration being operative to seize said walls of said cavity;

inserting said second portion of said instrument into said cavity; and deforming said second portion into said second configuration and seizing said walls of said cavity;

wherein the step of providing further comprises the step of:

providing a guiding device for guiding said instrument through non-straight body cavities, said guiding device substantially preventing deformation of said second portion when in said first configuration and being removable so as to permit deformation of said second portion when in said second configuration;

and wherein prior to the step of deforming, said guiding device is removed from said second portion to permit deformation of said second portion.

* * * * *